United States Patent [19]
Takemoto et al.

[11] Patent Number: 5,683,082
[45] Date of Patent: Nov. 4, 1997

[54] GAMING SYSTEM CONTROLLING TERMINATION OF PLAYING AND DEGREE OF PLAYING DIFFICULTY

[75] Inventors: Takatoshi Takemoto; Kazunari Kawashima, both of Tokyo, Japan

[73] Assignee: Kabushiki Kaisha Ace Denken, Japan

[21] Appl. No.: 381,843

[22] PCT Filed: Aug. 3, 1990

[86] PCT No.: PCT/JP93/01086

§ 371 Date: Feb. 3, 1995

§ 102(e) Date: Feb. 3, 1995

[87] PCT Pub. No.: WO94/03247

PCT Pub. Date: Mar. 17, 1994

[30] Foreign Application Priority Data

Aug. 4, 1992 [JP] Japan .................. 4-208124

[51] Int. Cl.[6] .................................................. A63F 7/40
[52] U.S. Cl. .................................. 273/121 B; 463/23
[58] Field of Search ................................ 463/23, 29, 18, 463/19, 20, 13, 10, 26, 25, 42, 40; 273/121 B

[56] References Cited

U.S. PATENT DOCUMENTS

| 4,657,247 | 4/1987 | Okada . | |
|---|---|---|---|
| 4,856,787 | 8/1989 | Itkis . | |
| 5,326,104 | 7/1994 | Pease et al. | 463/18 |
| 5,393,057 | 2/1995 | Marnell, II | 463/13 |

FOREIGN PATENT DOCUMENTS

| 52-112439 | 9/1977 | Japan . |
|---|---|---|
| 59-177084 | 10/1984 | Japan . |
| 59-225087 | 12/1984 | Japan . |
| 60-75072 | 4/1985 | Japan . |
| 60-135764 | 9/1985 | Japan . |
| 62-286489 | 12/1987 | Japan . |
| 63-24976 | 2/1988 | Japan . |
| 63-318982 | 12/1988 | Japan . |
| 1-52032 | 11/1989 | Japan . |
| 2-213374 | 8/1990 | Japan . |
| 3-80787 | 8/1991 | Japan . |
| 3-254775 | 11/1991 | Japan . |
| 3-254776 | 11/1991 | Japan . |
| 3-272790 | 12/1991 | Japan . |
| 4-132580 | 5/1992 | Japan . |
| 5-96058 | 4/1993 | Japan . |
| 2118809 | 11/1983 | United Kingdom . |

*Primary Examiner*—Jessica Harrison
*Assistant Examiner*—Michael O'Neill
*Attorney, Agent, or Firm*—Andrus, Sceales, Starke & Sawall

[57] ABSTRACT

In a gaming system comprising a plurality of gaming machines according to the invention, to raise diversity, pleasure, convenience, etc., of game plays, each gaming machine is provided with a game memory which stores various game programs and a game controller for executing a program read from the game memory in response to a game selection command, and a centralized controller is provided with a degree-of-difficulty adjustment section responsive to a game condition signal from each game controller for adjusting the degree of difficulty in playing a game executed by the game controller and a gaming machine termination controller for determining whether or not each gaming machine is to be terminated.

8 Claims, 20 Drawing Sheets

100 INPUT AMOUNT DETERMINATION PROCESS
101 GAME REMAINING AMOUNT DETERMINATION PROCESS
102 GAME SELECTION PROCESS  104 EXECUTE ONE GAME
1031 GAME REMAINING AMOUNT ≥ PLAY CHARGE
1038 GAME REMAINING AMOUNT ← GAME REMAINING AMOUNT
    −PLAY CHARGE
    DISPLAY GAME REMAINING AMOUNT

1032 TOTAL SCORE ≥ PLAY SCORE?
1037 TOTAL SCORE ← TOTAL SCORE −PLAY
    SCORE
    DISPLAY TOTAL SCORE
1033 DISPLAY MESSAGE OF INSUFFICIENT
    AMOUNT OF MONEY
1034 IS GAME SELECTION CHANGE SPECIFIED?
1035 IS GAME AMOUNT CHANGE SPECIFIED?
1036 IS INPUT AMOUNT CHANGE SPECIFIED?
1071 DISPLAY TERMINATION MESSAGE
1030 PERFORM ADJUSTMENT PROCESS

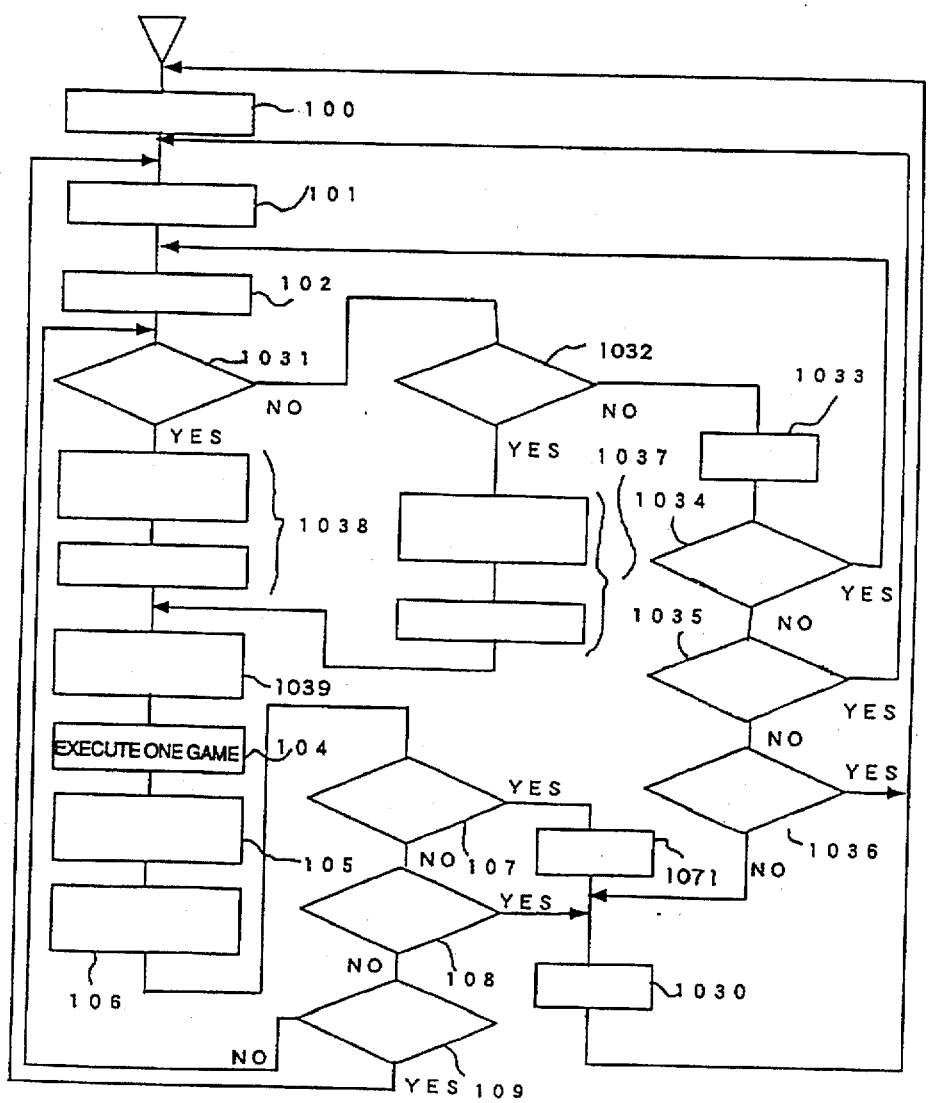

1039 DEGREE OF DIFFICULTY ← DEGREE OF DIFFICULTY +
    DEGREE-OF-DIFFICULTY CHANGE VALUE
105 UPDATE TOTAL SCORE AND DISPLAY UPDATED TOTAL SCORE
106 INQUIRE ABOUT DEGREE-OF-DIFFICULTY CHANGE VALUE
107 IS TERMINATION MESSAGE DISPLAYED?
108 ADJUSTMENT COMMAND?
109 CANCEL COMMAND?

FIG. 10

112 INPUT REMAINING AMOUNT. ≧ LOWEST PLAY CHARGE?
113 SCORE ≧ LOWEST PLAY SCORE
114 DISPLAY MESSAGE OF INSUFFICIENT AMOUNT OF MONEY
115 CANCEL COMMAND OR ADJUSTMENT COMMAND ?
116 PERFORM ADJUSTMENT PROCESS

GAMING SYSTEM CONTROLLING TERMINATION OF PLAYING AND DEGREE OF PLAYING DIFFICULTY

TECHNICAL FIELD

This invention relates to a gaming system comprising a centralized controller and at least one gaming machine connected to the centralized controller by a line and gaming machines used with the gaming system.

TECHNICAL BACKGROUND

Generally, in gaming houses such as pinball halls, a player can play only one type of game, such as a pinball or slot machine, at each gaming machine.

To prevent players from losing the enjoyment of playing games, the degree of difficulty in playing games at each gaming machine is preferably adjusted appropriately in response to how the players win games, etc., at the gaming machine. However, it requires a great deal of labor and is not practical to make such adjustment manually for each game for all gaming machines.

Thus, enhancing the diversity, enjoyment, convenience, etc., of playing games is limited.

The player can still play only one type of game at one gaming machine; he or she cannot select one among various games. To provide diversified games, the gaming house must contain a large number of gaming machines, which requires a large location and enormous costs.

If the degree of difficulty in playing games is not adjusted, if it is much too difficult for players to win games, they may not enjoy playing games, while if it is much too easy for players to win games, they may lose interest in playing games. Thus, the players can preferably win games at a given degree of difficulty, but if every gaming machine is adjusted to a given degree of difficulty, the players may or may not be able to win games at a desirable degree of difficulty depending on their skill in playing games.

DISCLOSURE OF INVENTION

It is therefore an object of the invention to provide a gaming system which enables a player to play various games at a gaming machine by selecting one of the games, and gaming machines used with the gaming system. It is another object of the invention to provide a gaming system which adjusts the degree of difficulty in playing a game at each gaming machine in response to the game score condition and gaming machines used with the gaming system. It is a further object of the invention to provide a gaming system which controls termination of gaming machines in response to the score and the degree of difficulty and gaming machines used with the gaming system. It is another object of the invention to provide a gaming system which can execute batch management of gaming machine termination control and degree of difficulty setting by a centralized controller, and gaming machines used with the gaming system.

To these ends, according to the invention, there is provided a gaming system comprising a centralized controller and at least one gaming machine connected to the centralized controller by a line, characterized in that the gaming machine comprises:
a controller for controlling the gaming machine, a game image display unit for outputting a game image, and an operation section for accepting various operation commands input by a player for playing a game, the controller having a storage and a CPU,
the CPU comprising a game controller for controlling a game; an image display controller for outputting information, as instructed from the game controller, to the game image display unit; and a game interface for sending commands input to the operation section to the game controller,
the game controller comprising means for determining the degree of difficulty in playing a game; means for executing a game at the degree of difficulty; and means for informing the centralized controller of game conditions, and that
the centralized controller comprises a controller,
the controller comprising means for accepting input of a game condition; means responsive to the accepted game condition for determining a degree-of-difficulty change value used to determine the degree of difficulty; and means for informing the game controller of the determined degree-of-difficulty change value.

Thus, termination of the gaming machines can be controlled in response to the score and the degree of difficulty.

Preferably, the controller of the centralized controller in the gaming system of the invention further includes means responsive to the accepted game condition for determining whether or not the gaming machine is to be terminated and means for sending a termination instruction to the game controller in response to the determination of termination, and the game controller has means for terminating the gaming machine upon receipt of the termination instruction.

Thus, the gaming machines can be terminated in response to the game condition.

The storage of the gaming machine may have a game program storage area, the operation section may have means for accepting selection of a game type and informing the game controller of the selected game type, and the game controller may have means for reading a game program previously stored in the storage corresponding to the game of the type selected and executing it. Thus, any registered game program can be read from the storage of the gaming machine, shortening the time required for reading the game program. Since the centralized controller is not requested to send game programs, the processing load of the centralized controller can be reduced. If game type selection is accepted and the selected game is executed as described above, the player can play various games by selecting one of the games.

On the other hand, a storage of the centralized controller may have a game program storage area, the operation section may have a function of accepting selection of a game type and informing the game controller of the selected game type, the game controller may have means for requesting the centralized controller to send a game program of the game of the type selected, and the controller of the centralized controller may have means responsive to the request for reading the game program previously stored in the game program storage area and transmitting the game program to the game controller. The game controller may have means for executing the transmitted game program. Thus, the game program storage locations are unified in the system, facilitating maintenance of the game programs.

Further, each of the storages of the centralized controller and each gaming machine may have a game program storage area. Thus, frequently used game programs can be stored in the storages of the gaming machines and less frequently used game programs can be stored in the storage of the centralized controller for shortening the average required time for reading a game program and facilitating replacement of less frequently used programs.

Preferably, the centralized controller further includes an input unit, a storage of the centralized controller has a termination gaming machine table for registering the gaming machine to be terminated, and the controller of the centralized controller further includes means for sending a termination instruction to the game controller of the gaming machine registered in the termination gaming machine table and means for accepting specification of the gaming machine to be terminated from the input unit and registering the gaming machine in the termination gaming machine table. Thus, any desired gaming machine can be terminated from the centralized controller.

Preferably, the centralized controller further includes an input unit, a storage of the centralized controller has a degree-of-difficulty setup value storage area for registering a degree-of-difficulty setup value, and the controller of the centralized controller further includes means for determining a degree-of-difficulty change value so that the degree of difficulty becomes a degree-of-difficulty setup value stored in the degree-of-difficulty setup value storage area and means for accepting specification of a degree-of-difficulty setup value from the input unit and storing it in the degree-of-difficulty setup value storage area. Thus, the degree of difficulty can be set for all gaming machines by one operation of inputting the degree-of-difficulty setup value to the centralized controller.

According to the invention, there are provided gaming machines used with the gaming system.

BRIEF DESCRIPTION OF THE DRAWINGS

In the accompanying drawings:

FIG. 10 is a flowchart showing the processing contents of a game controller;

BEST MODE FOR CARRYING OUT THE INVENTION

Referring now to the accompanying drawings, there are shown embodiments of the invention.

Embodiment 1

Figure 7:
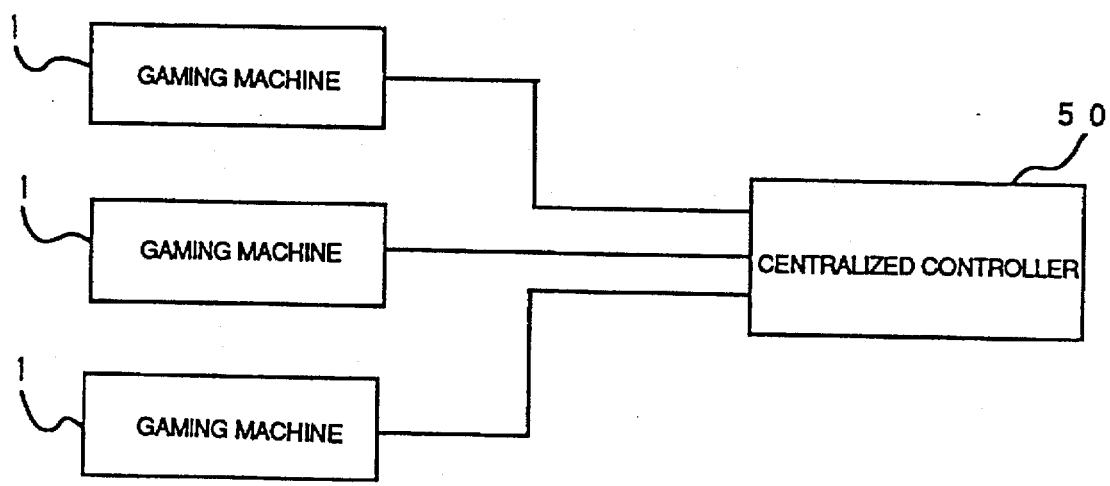
FIG. 7 is a block diagram showing the configuration of a gaming system of the invention.

A gaming system of a first embodiment comprises a centralized controller 50 for controlling gaming machines and at least one gaming machine 1 connected to the centralized controller via a line (communication line that can be used for transferring signals whether by wire or radio), as shown in FIG. 7 wherein a system having three gaming machines 1 is illustrated as an example.

The gaming machine according to the embodiment contains a controller 8, a card processor 5a, and a money processor 5b. It also has a game image display unit 11 for displaying a game image, an operation section 5, and a display unit 10 for displaying a game name and a score. The controller 8 has a storage 6 and a central processing unit (CPU).

The storage 6 stores information such as constants required for CPU operations. Also, the storage 6 comprises a game memory 12 which stores program information of games that can be played by players at the gaming machine 1. Programs of a number of types of video, pinball, and slot machine games are registered in the gaming machine 1 of the embodiment. When a player selects one of the game types, the gaming machine 1 accepts the selection and enables the player to play a game of the type selected. For example, a memory such as an IC card, semiconductor memory, optical disk (CD), digital magnetic tape (DCC), or magnetic disk (MD) can be used as the game memory 12.

The CPU has a game controller 14, a game interface 16, and an image display controller 15.

The game controller 14 reads a game program from the game memory 12 of the storage 6, makes the game of the type selected progress based on player input information obtained through the game interface 16, and informs the image display controller 15 of image information concerning the progress condition, etc. When making the game progress, the game controller 14 executes the game at the degree of difficulty received from the centralized controller 50 via the line 9. The game controller 14 sends information concerning the game progress condition, etc., to the centralized controller 50 via the line 9. The game progress condition signal includes data representing the so-called slump degree such as winning game play frequency. Further, the game controller 14 displays information such as the game name and score in information display areas of the display unit 10. The game controller 14 accepts information from the card processor 5a and the money processor 5b and controls the operation of the processors 5la and 5b.

The game controller 14 also transmits management data including the amount of money input to the gaming machine, the type of game played at the gaming machine, the game execution time, etc., together with the game condition signal to the centralized controller 50 via the line 9.

The game interface 16 accepts player input for selection of the game type, game progress, etc., through the operation section 5 and sends the input to the game controller 14.

The image display controller 15 controls display of the game image display unit 11 based on image information input from the game controller 14. Each of the image display controller 15 and the game controller 14 can be made of a microcomputer having a CPU, ROM, and RAM, for example.

Figure 3:
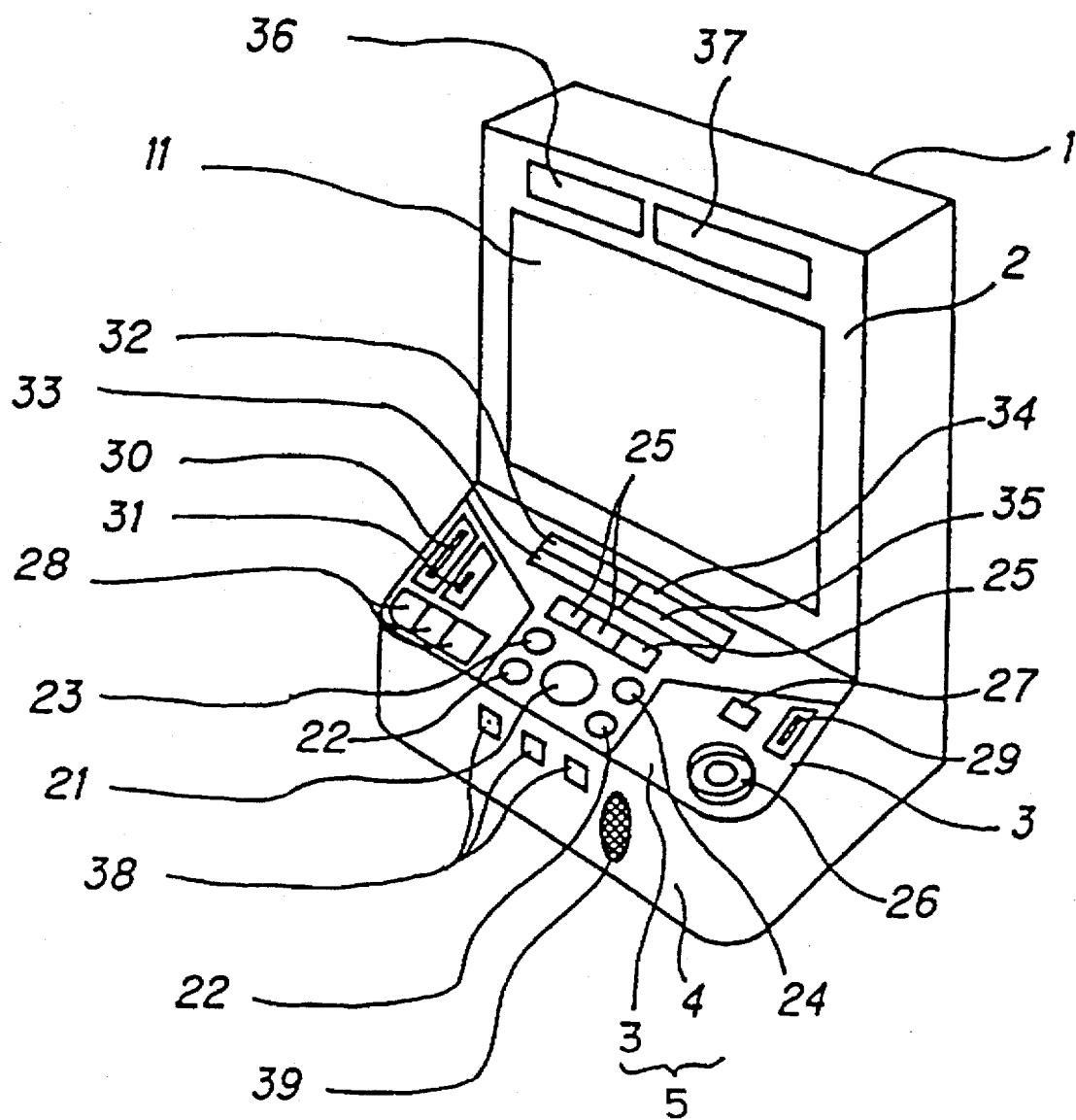
FIG. 3 is a perspective view showing the appearance of the gaming machine with a game image display unit placed in a vertical position.

FIG. 3 shows the appearance of the gaming machine 1 according to the embodiment. The game image display unit 11 for displaying a game image is provided on the front 2 of the gaming machine 1. The embodiment uses a panel display, such as a liquid crystal display screen, as the game image display unit 11, but a CRT can also be used. However, a liquid crystal display screen is preferably used because the display unit can be then made small.

Figure 8:
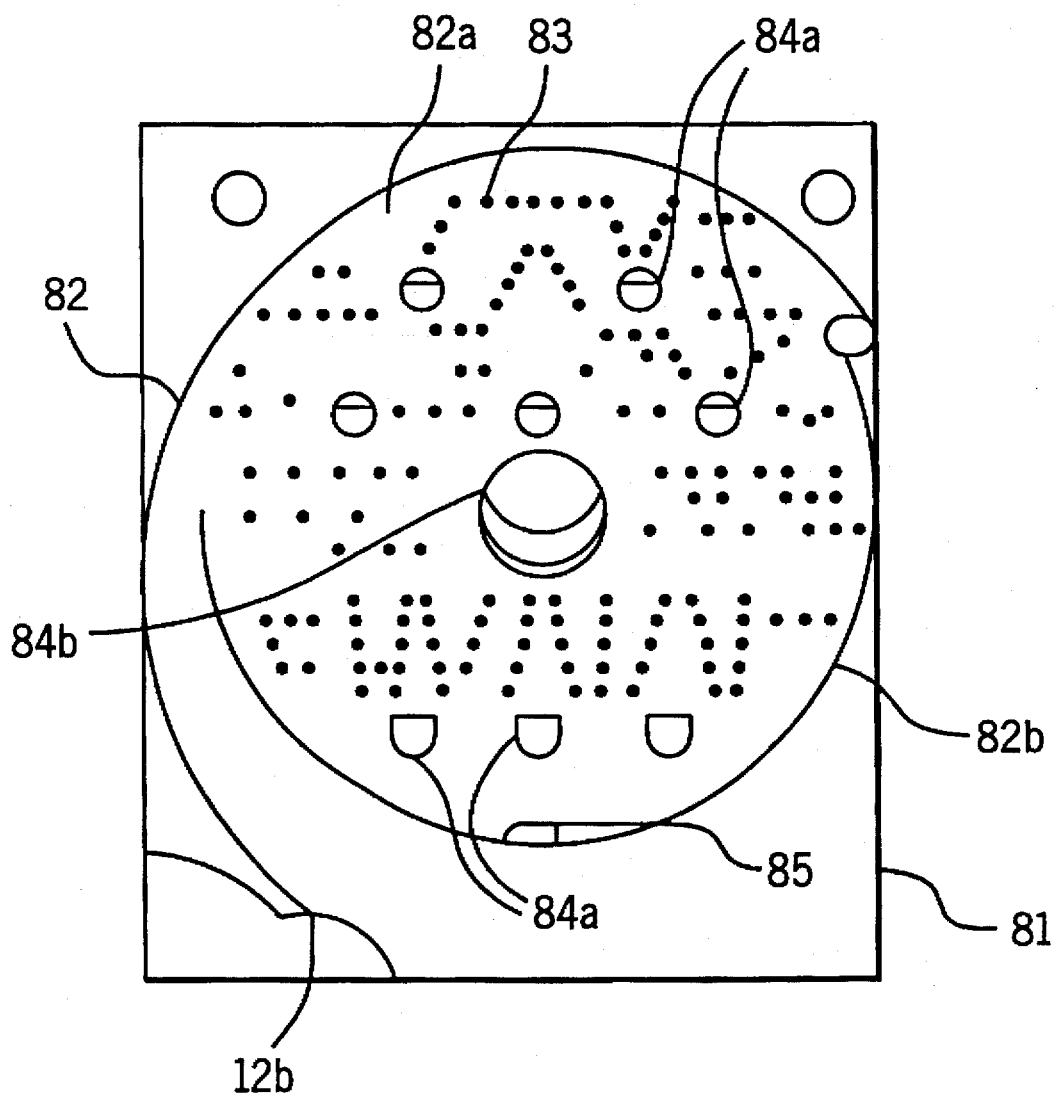
FIG. 8 is an illustration showing an example of a display screen output when a pinball game is executed.
Figure 9:
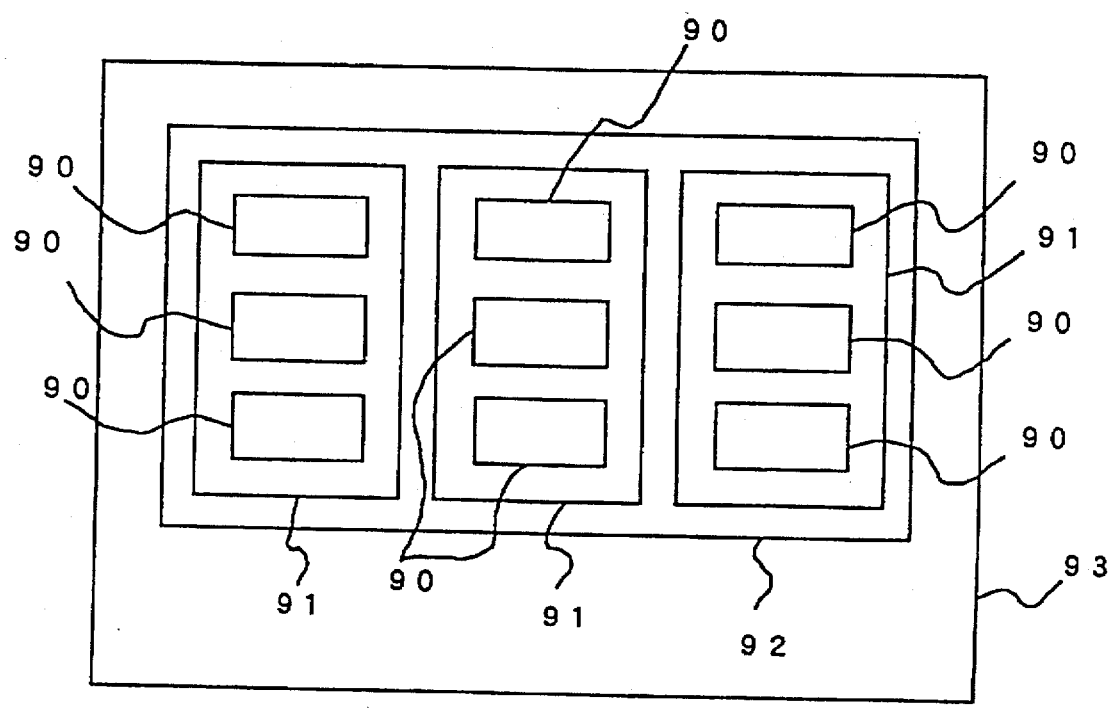
FIG. 9 is an illustration showing an example of a display screen output when a slot machine game is executed.

FIGS. 8 and 9 show examples of display screens of the game image display unit 11 displayed by the image display controller 15.

FIG. 8 is an example of a display screen output when a pinball game is played. A guide rail 82 and a lower guide rail 82b are provided on a base board 81. The inner area surrounded by the guide rail 82 and the lower guide rail 82b within the base board 81 provides a game area 82a. The image of a pinball displayed as if it were propelled from the lower left portion 12b of the base board 81 is displayed as if it moved to the vertical upper position (upstream) of the game area 82A along the guide rail 82.

The pinball image is displayed as if the pinball rose upstream along the guide rail 82 while decelerating due to gravity. The speed from when the pinball is propelled, changes to fall at speed 0, and the ball then drops while accelerating due to gravity. The pinball image is displayed as if the pinball fell to the lower guide rail 82b, then moved toward the downstream center of the base board along the rail 82b, entered an out hole 85, and disappeared from the base board.

In the game area 82b of the base board 81, images of a large number of pins (nails) 83 are displayed so that a pinball falling along the base board 81 frequently collides with the pins and it's direction of movement is made to fluctuate. When an obstacle, such as the pin 83 or the lower guide rail 82b, exists in the way of falling pinball, the pinball image is displayed as if the pinball collides with the obstacle and changes movement direction.

The game area 82a is provided with the three types of regions displayed as if the pinball image entered the hole and disappeared from the base board 81 (displayed as if holes were made): A plurality of safe holes 84a— if a player enters the pinball image in the hole, they win the game—, a win effect indication 84b provided at the base board center from upstream to downstream—if the pinball image enters the hole, a special win condition is provided—, and the out hole 85 displayed as if pinballs not entering the safe holes 84a were finally collected and discharged from the base board 81. When the player enters the pinball image in the safe hole, they are given predetermined points for the winning game play.

The state of the win effect indication 84b changes each time the pinball image enters a specific safe hole 84a. If the player satisfies a predetermined condition, a large number of pinballs are paid out to the player for the winning game play. For example, slots like those of a slot machine are displayed and reels are displayed as if they rotated each time the player wins a game. If a predetermined symbol pattern is completed when the reel rotation stops, a special win condition is entered and a large safe hole (not shown) appears downstream to allow the pinball image to easily enter the safe hole. When a win condition or a special win condition is set, color or the like on the base board 81 can also be changed for informing the player of a condition change.

FIG. 9 is an example of a display screen output on the game image display unit 11 when a slot machine game is played. A sideways oblong area 92 is displayed on the display screen 93. Three longwise rectangular areas (slots) 91 are displayed in the area 92. Three symbols 90 can be displayed vertically within each slot 91. That is, a maximum of nine symbols (three rows x three columns) are displayed on the display screen 93.

When a game is started, display is made in each slot 91 as if the symbols 90 were drawn continuously on each reel and the reels rotated. When the game end is specified, the rotation display is terminated and the three symbols 90 are displayed in each slot. If the same symbols 90 are displayed at a position determined in each slot in response to the input amount of money, the completed symbols 90 are highlighted and a point is added. The determined position is previously defined as a horizontal row only at the intermediate stages of the slots, for example, when one coin is input, a horizontal row at any of upper, intermediate, and lower stages when two coins are input, or a horizontal row at any of upper, intermediate, and lower stages or a slant row when three coins are input.

As shown in FIG. 3, the display unit 10 of the gaming machine 1 according to the embodiment has the six display areas: An upper game name display area 36 and an upper score display area 37 above the game image display unit 11, and a lower game name display area 34, a lower score display area 35, an input remaining amount display area 32, and a game remaining amount display area 33 below the game image display unit 11.

The input remaining amount display area 32 is an area for displaying the remaining amount of the input money not yet spent for playing games. The game remaining amount display area 33 is an area for displaying the remaining amount of money specified to be used for playing games. Each of the lower and upper game name display areas 34 and 36 is an area for displaying the specified game type name. Each of the lower and upper score display areas 35 and 37 is an area for displaying the game score. The display areas 32 to 37 are provided by liquid crystal display devices in the embodiment. A part of one liquid crystal display screen may be used as the game image display unit 11 and the remaining display portion may provide the six display areas.

The operation section 5 consisting of a slant plane 3 and a vertical plane 4 on the front of the bottom is provided below the game image display unit 11; it comprises various operation components. The operation components placed on the slant plane 3 include a main switch 21, game switches 22, a setting switch 23, a cancel switch 24, game amount selection switches 25, a handle 26, an adjustment switch 27, number-of-input-coins selection switched 28, a card inlet/outlet 29, a bill slot 30, and a coin slot 31. The input remaining amount display area 32, the game remaining amount display area 33, the lower game name display area 34, and the lower score display area 35, which are display areas of the display unit, 10 are also provided on the slant plane 3. The operation components provided on the vertical plane 4 include game end switches 38 and a loudspeaker 39.

If a touch section is provided, all or some of the operation switches on the operation section 5 (the main switch 21, game switches 22, setting switch 23, cancel switch 24, game amount selection switches 25, handle 26, adjustment switch 27, number-of-input-coins selection switches 28, and game end switches 38) can also be defined as an area on the one touch section.

In this case, all or some of the switches may be previously defined on the touch section, but the switches to be defined may be changed in response to the operation progress condition and the game type. For example, first the game type selection switches are defined as an input area on the touch section, and when a touch of the area is sensed, the switch input is accepted. When a player specifies the game type, then the switches required for the player to specify an amount of money spent for the game to play are defined as an input area on the touch section. When the player specifies the amount of money, the game progress and stop switches are defined as an input area on the touch section. When the player ends the game, an adjustment switch is defined. Thus, the switches may be defined on the touch section in response to the operation progress condition in such a manner.

The switches defined on the touch section can also be changed in response to the type of game to be played. That is, for slot machine or pinball games for which the main switch 21 and the game switches 22 are not used, definition of these switches 21 and 22 may be skipped, and for games for which only the main switch 21 is used without using the game switches 22, the handle 26, or the game end switches 38, definition of these switches 22, 26, and 38 may be omitted.

Next, the switches, etc., on the operation section 5 will be discussed.

The switches used for accepting selection of the type of game to be played are the setting switch 23 and the cancel switch 24. Players use the setting switch 23 to enter final specification of a game during a game selection operation, and use the cancel switch 24 to change game specifications during the game selection operation.

The switches for accepting input concerning video game progress are the main switch 21 and the game switches 22. The main switch 21 is provided to accept input of commands for moving a cursor and characters, scrolling the screen, etc., during game operation. The main switch 21 is mainly used when video games are played. The main switch 21 is also used to move the cursor during the game selection operation. The embodiment uses a roll ball as the main switch 21, but the main switch can also be made of an input device such as a joystick or a fixed mouse. The game switches 22 are used as auxiliary switches of the main switch 21 when a game is being played; in the embodiment, two game switches are provided.

The switches used for game operation in pinball or slot machine games are the handle 26 and the game end switches 38. The handle 26 serves as a pinball propelling handle when players play pinball games; it functions as a game start switch when players play slot machine games. If the specified game is a slot machine game, the game end switches 38 are used to accept a command for ending the game, namely, stopping reel rotation display in the slots.

The gaming machine 1 of the embodiment has a game progress function in response to the input of money. The game amount selection switch 25 is a switch for accepting specification of the amount of money to be spent for the game to be played. The adjustment switch 27 is a switch for accepting an adjustment process command at the game end. When receiving an input from the adjustment switch 27 via the game interface 16, the game controller 14 performs an adjustment process described below. When players input gaming medals or coins (hereinafter only referred to coins) for playing a game, the number-of-input-coins selection switched 28 serves as a switch for accepting specification of the number of coins to be spent for the game to be played.

The gaming machine 1 of the embodiment can accept input of money in any form, namely a prepaid card, coins, or bills. To accept input of money, the gaming machine 1 is provided with the card inlet/outlet 29, the coin slot 31, and the bill slot 30.

The card inlet/outlet 29, which is used to receive and dispense a prepaid card used in place of cash or to dispense an adjustment card, is connected to the card processor 5a (not shown in FIG. 3) provided in the gaming machine. The card processor 5a has a magnetic card drive having read and write functions, for example; it reads the amount data recorded on a magnetic card input through the card inlet/outlet 29 and sends it to the game controller 14 at the appropriate time. At the time of adjustment, it has a function of writing data of the remaining amount, the number of finally won pinballs, etc., onto the card and then dispensing the card.

The card processor 5a contains a magnetic card stack section (not shown) for holding a plurality of magnetic cards and a card dispensing mechanism (not shown). If a game is started with only cash or gaming medals input without a magnetic card, at the time of adjustment the data of the remaining amount, the number of finally won pinballs, etc., can be written onto one of the magnetic cards held in the stack section and the card then dispensed.

The card processor 5a allows not only magnetic cards, but also receipts or the like on which data is visually recorded, to be used as input/output media. For example, a card processor may be used which uses magnetic cards only as card-like recording media for inputting amount data and receipts or the like on which data is printed, or for outputting data of the number of finally won pinballs. Also, a card processor may be used which uses recyclable cards on which characters, etc., can be represented and erased as a result of a temperature change (cards proposed by the applicant in Japanese Patent Application No. Hei 3-260879) as card-like recording media.

The bill slot 30 and the coin slot 31, which are provided for players to input bills and coins for playing games, are connected to the money processor 5b (not shown in FIG. 3) provided in the gaming machine. The money processor 5b has a validator (not shown) for determining the denomination and number of coins inserted through the coin slot 31 and a validator (not shown) for determining the denomination and number of bills inserted through the bill slot 30. Each time a coin or bill is input, the money processor 5b sends a signal corresponding to the denomination of the coin or bill to the game controller 14, which then uses it as data required for calculating the input amount of money.

In this case, the slot 31 is a slot for coins and the slot 30 is a slot for bills and the validator is provided for each of the slots. Input bills are stored in the gaming machine in the embodiment, but a transport line of bills, etc., may be disposed on the rear of the gaming machine 1 for automatically transporting them to a stacker, a money changing machine, etc., placed at the end of a row of gaming machines on the transport line.

The loudspeaker 39 produces a sound effect during a game or a beeping sound or the like for informing the player that an input error has been made, etc., during game selection and the like. Preferably, the loudspeaker 39 produces a sound so as not to disturb other players. For example, it may be placed at the side of a player's head or attached to a seat.

Not all of the operation components need necessarily be provided on the gaming machine 1. For example, they may be mounted on a separate operation box that can be taken out from the armrest of a player's seat toward the player, namely, a remote control system may be adopted.

Figure 6:
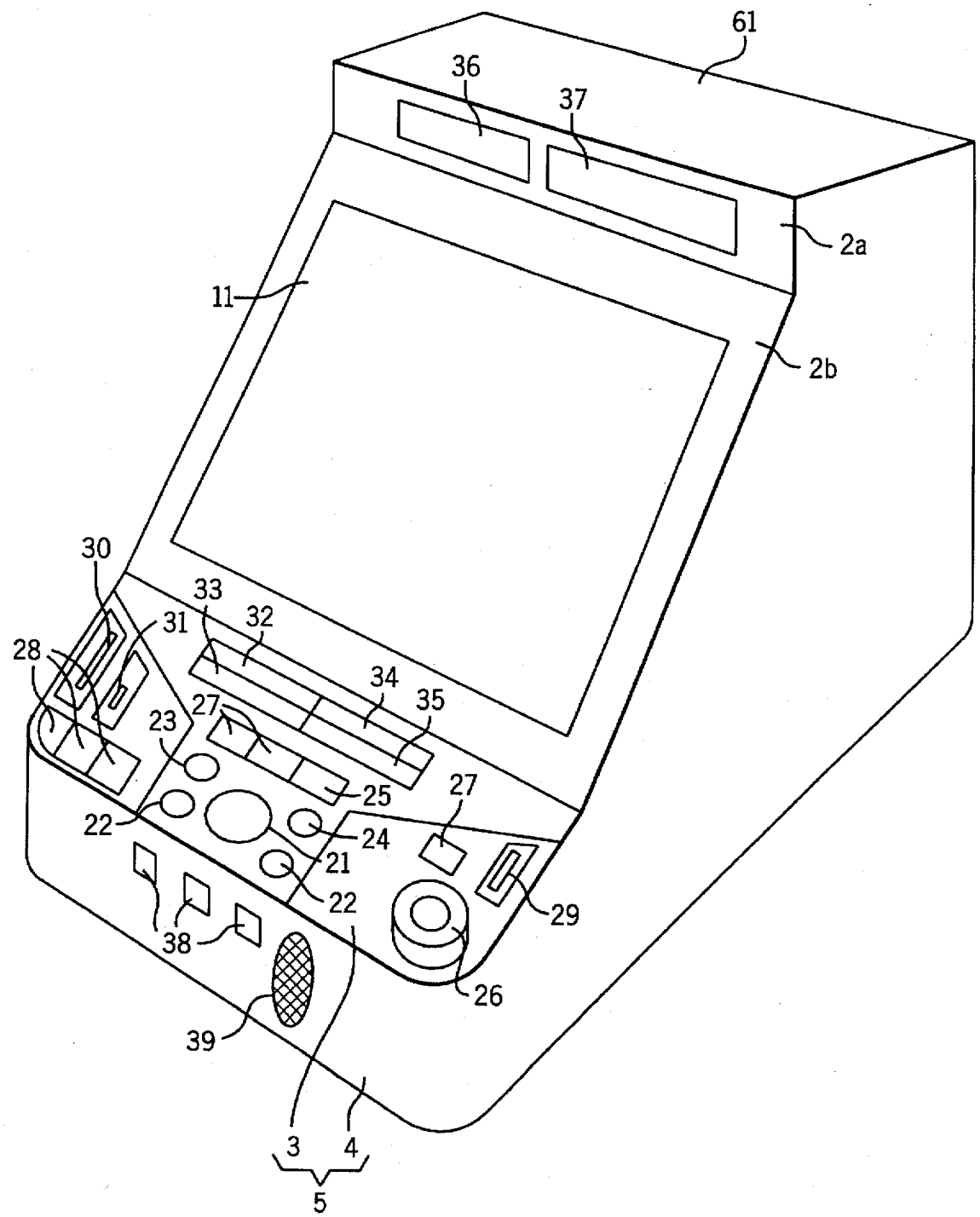
FIG. 6 is a perspective view showing the appearance of the gaming machine with a game image display unit inclined.

The gaming machine 1 may take a form in which almost all of the front portions, except for a vertical plane 2a on the top providing the upper game name display area 36 and the upper score display area 37, are inclined forward, as shown in FIG. 6. In this case, the game image display unit 11 can also be formed on the inclined plane 2b on the front. Such a form would enable players to easily view the game image display unit depending on the lighting position, the gaming machine size, etc.

Next, the components of the centralized controller 50 will be discussed.

Figure 1:
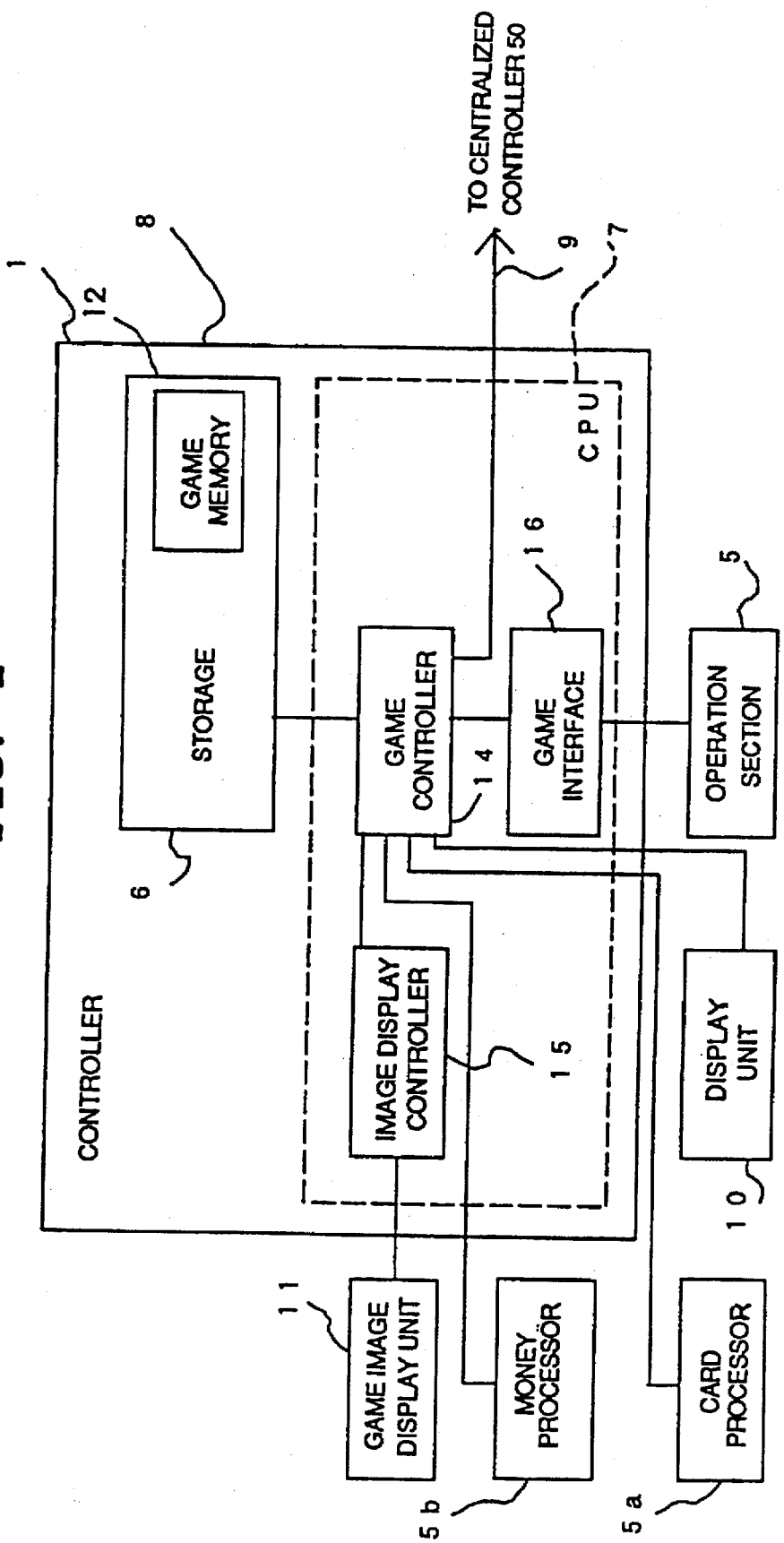
FIG. 1 is a block diagram showing the configuration of a gaming machine having a game memory.
Figure 2:
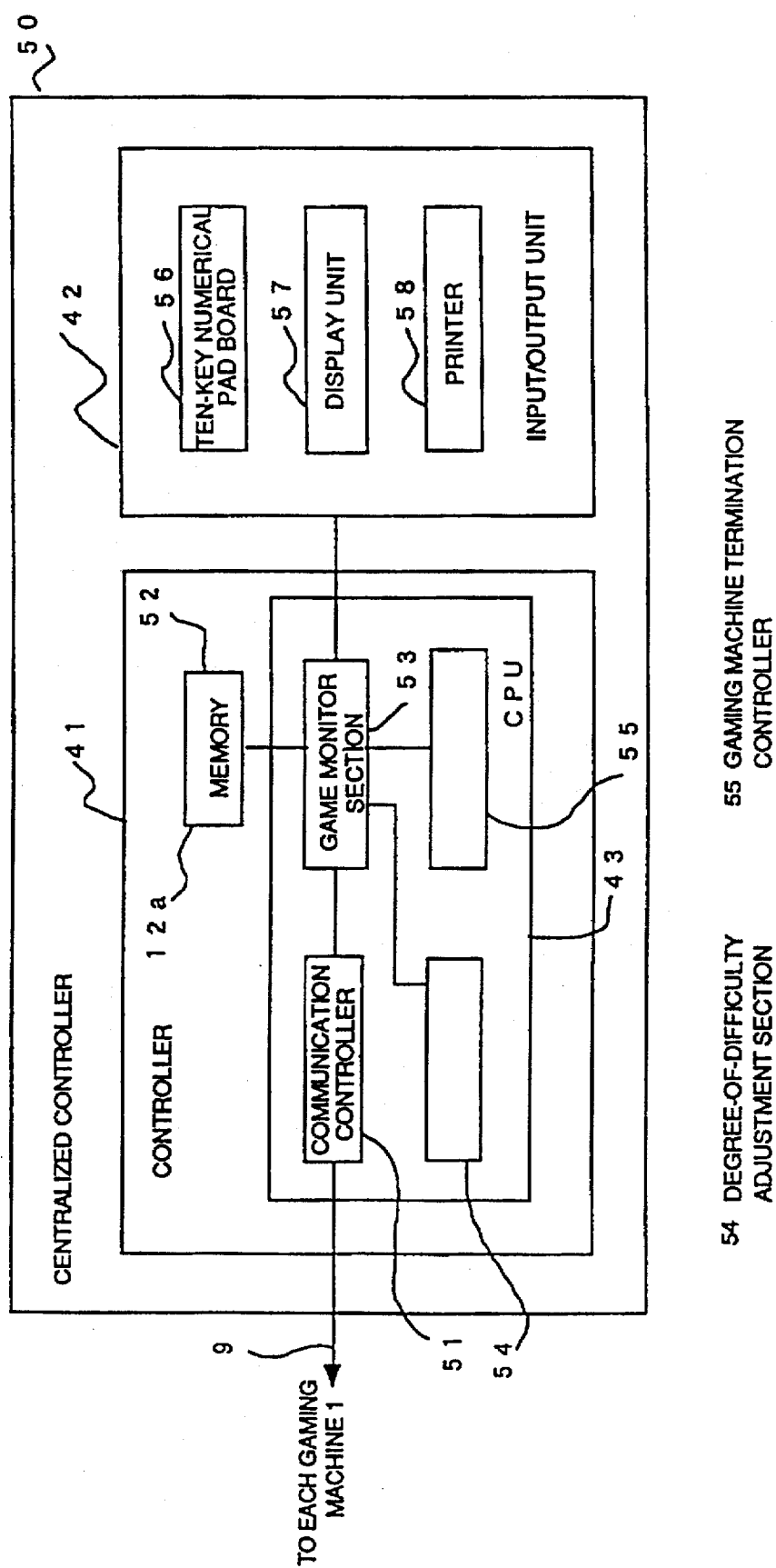
FIG. 2 is a block diagram showing the configuration of a centralized controller having no game memory.

The centralized controller 50 has a controller 41 and an input/output unit 42, as shown in FIG. 2. The controller 41 has a memory 52 and a CPU 43 which comprises a communication controller 51, a game monitor section 53, a degree-of-difficulty adjustment section 54, and a gaming machine termination controller 55.

The memory 52 has a storage area of history data of each gaming machine 1. The history data is provided by accumulating data of the type of game played, execution time, score, degree of difficulty, determined degree-of-difficulty change value, etc., and data as to whether or not the gaming machine is terminated for each game. Further, the memory 52 has a termination gaming machine table storage area in which terminated gaming machines are registered. The memory 52 also has a termination limit value storage area which stores the termination limit value used for determining whether or not the gaming machine is to be terminated for each game type, a degree-of-difficulty setting flag storage area which stores a degree-of-difficulty setting flag indicating that a degree-of-difficulty setup value is set, an area which stores the degree-of-difficulty setup value to set the degree of difficulty, an area which stores the degree-of-difficulty upper limit value used for determining whether or not the gaming machine is to be terminated, and an area which stores a reference score used to find a degree-of-difficulty change value. The memory 52 also holds data used for operations carried out by the game monitor section 53, the degree-of-difficulty adjustment section 54, and the gaming machine termination controller 55. For example, the data includes information as to which of the time and score the termination limit value is represented by. The game monitor section 53 registers and reads information in and from the memory 52. The input/output unit 42 has a ten-key numerical pad board 56, a display unit 57, and a printer 58.

Figure 20:
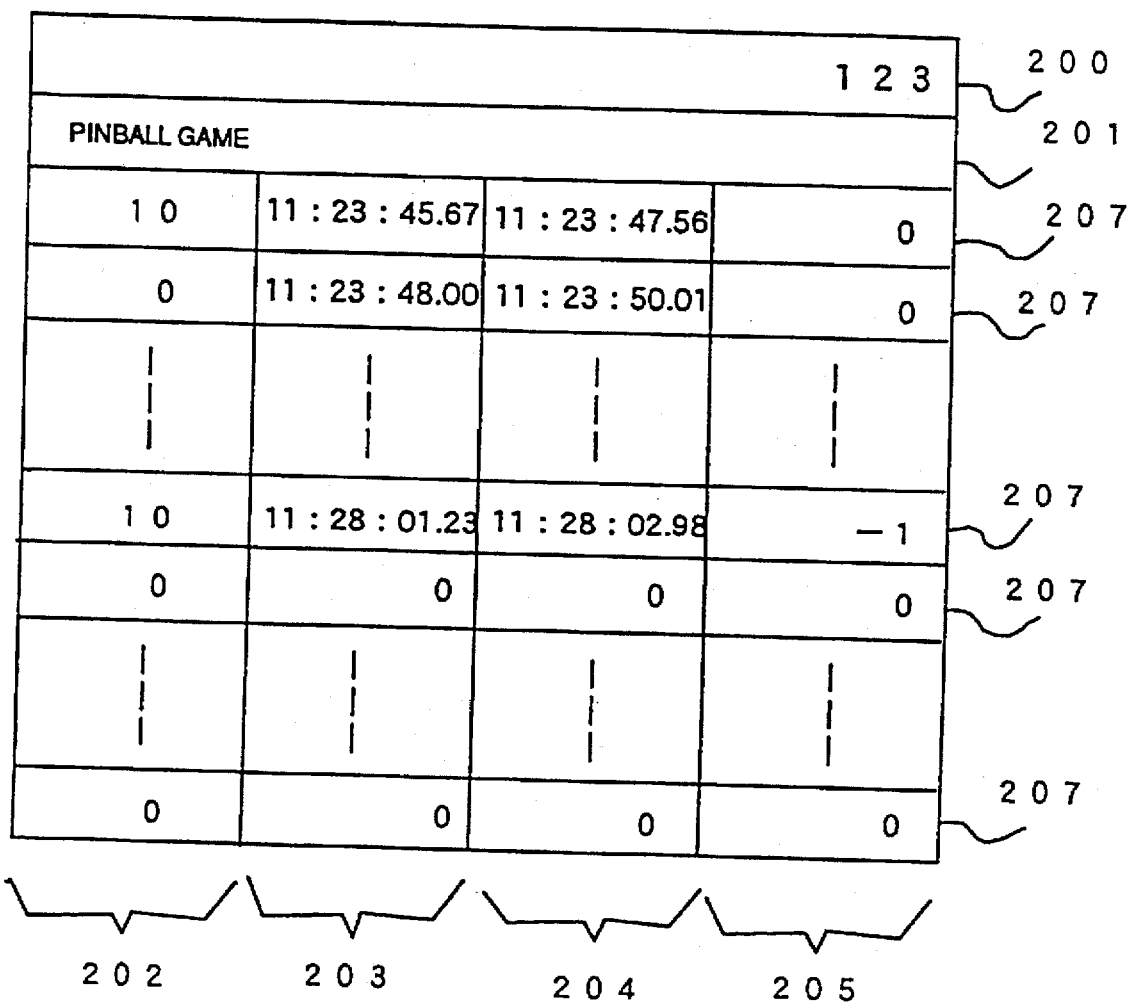
FIG. 20 is a data format showing an example of history data.

FIG. 20 shows an example of the history data. In the embodiment, the history data storage area comprises a number-of-game-play-times storage area 200, a game type storage area 201, and a large number of game data storage areas 207. Each game data storage area 207 consists of a score storage field 202, a play start time storage field 203, a play end time storage field 204, and a degree-of-difficulty storage field 205. Data is stored in as many game data storage areas 207 as the number of times a game has been played, held in the number-of-game-play-times storage area 200 (123 times in the example shown in FIG. 20). The initial value 0 is stored in the remaining game data storage areas 207.

The communication controller 51, which is connected to the game controller 14 of each gaming machine 1 via the line 9 for communication, performs communication control, such as necessary signal format conversion, for transferring signals such as commands and data to and from the gaming machines 1.

The game monitor section 53 receives information about game conditions, etc., via the communication controller 51 from the game controller 14 of each gaming machine 1, and sends the information to the degree-of-difficulty adjustment section 54 or the gaming machine termination controller 55. When receiving a game degree-of-difficulty change value from the degree-of-difficulty adjustment section 54, the game monitor section 53 sends the degree-of-difficulty change value via the communication controller 51 to the gaming machine 1 for which the degree of difficulty is to be changed. When receiving a command for terminating the game from the gaming machine termination controller 55, the game monitor section 53 instructs the corresponding gaming machine 1 to terminate the current game being played.

The degree-of-difficulty adjustment section 54 determines the game degree-of-difficulty change value based on the game condition information received from the game monitor section 53, and sends it to the game controller 14.

The gaming machine termination controller 55 determines whether or not the game is to be terminated, based on the game condition information received from the game monitor section 53, and sends the determination result to the game monitor section 53.

The game monitor section 53, the degree-of-difficulty adjustment section 54, and the gaming machine termination controller 55 can be provided by a microcomputer comprising a CPU, ROM, and RAM, for example.

The ten-key numerical pad board 56 is a device capable of accepting input of numeric values of 0-9. The embodiment uses the keyboard having ten keys 0-9, but any other input device such as a mouse or a light pen may be used. If the display unit 57 is used as a touch section and an input area is previously defined for enabling numerical value input, the ten-key numerical pad board 56 as in the embodiment need not be provided.

The display unit 57, which has a liquid crystal display screen, outputs information to the screen as instructed by the game monitor section 53. It can also be used as a touch section, as described above. The display unit 57 may use other display screens such as a CRT.

The printer 58 is a device for printing out information as instructed by the game monitor section 53. Either of the display unit 57 and the printer 58 may be omitted. To omit the display unit 57, all output information from the game monitor section 53 should be printed out on the printer 58. However, if the display unit 57 is omitted, information which need not be saved is also printed out, making information difficult to see and wasting paper. If the printer 58 is omitted, output information cannot be saved. Therefore, both devices are provided preferably.

I. Process flow of gaming machine 1

Next, a process flow of the gaming machine 1 will be described. FIG. 10 is a flowchart showing a process outline of the game controller 14.

(1) Input amount determination process (step 100)

The game controller 14 determines the amount of money that can be spent for the game to be played using an input amount determination process at step 100. The amount of money means the amount of money input by means of bills, coins, or a card, or the number of game play media such as gaming medals.

Figure 11:
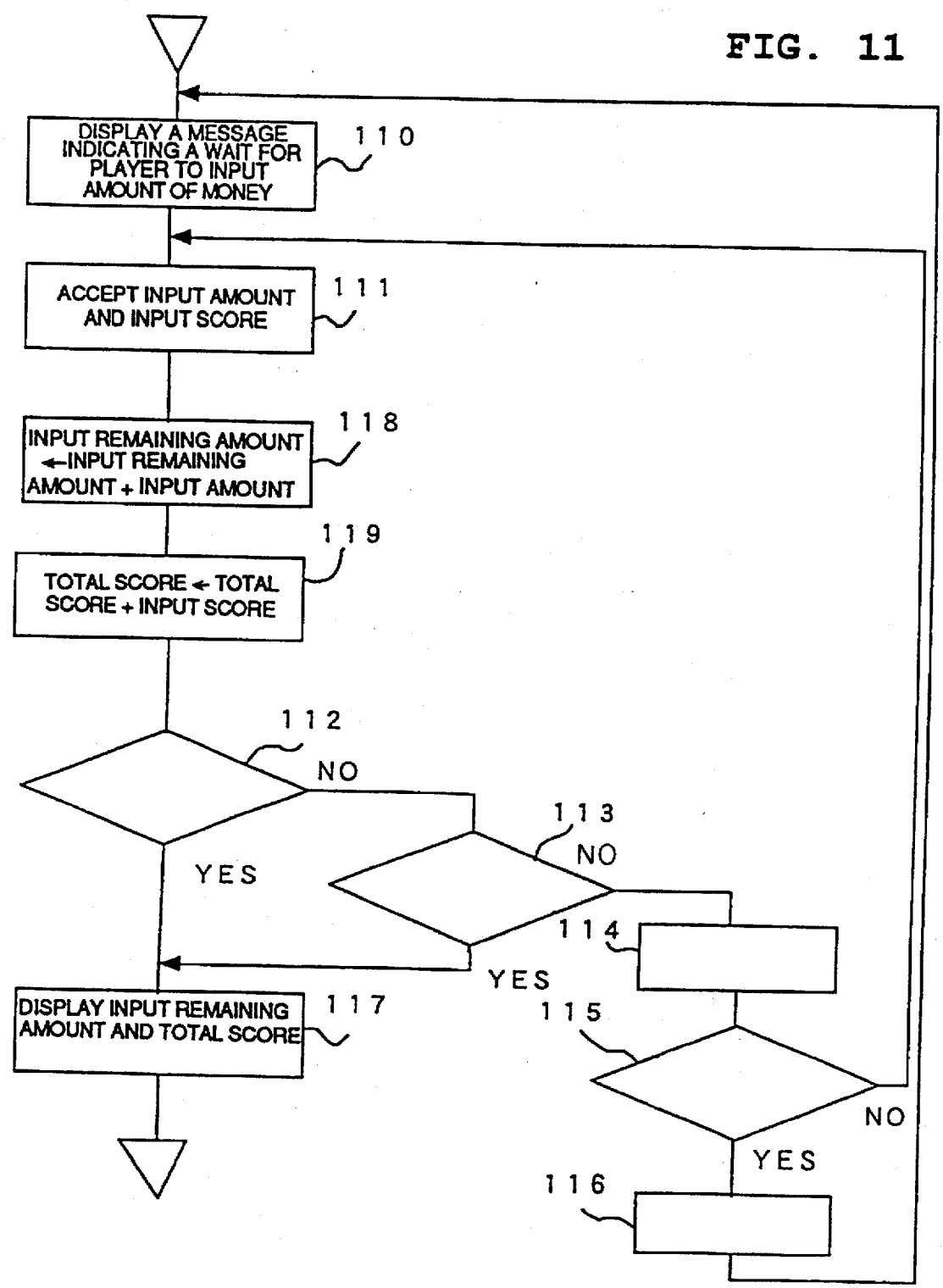
FIG. 11 is a flowchart showing an input amount determination process of the game controller.

FIG. 11 shows a flow of the input amount determination process. The game controller 14 displays a message, indicating a wait for a player to input an amount of money, on the game image display unit 11 through the image display controller 15 at step 110. At this time, the game controller 14 displays the input remaining amount, game remaining amount and score in the input remaining amount display area 32, the game remaining amount display area, and upper and lower score display areas 37, 35, respectively, on the display unit 10. The initial values displayed in the areas are 0.

Next, the game controller 14 waits for receipt of the input amount and input score from the card processor 5a or receipt of the input amount from the money processor 5b. Then, the game controller 14 totals the input amounts and the input score received within a given time at step 111, adds the sum of the input amounts to the input remaining amount at step 118, and adds the score to the total score at step 119.

When a predetermined magnetic card is inserted into the card inlet/outlet 29 on the operation section 5, the card processor 5a reads the amount of money and the score registered on the inserted magnetic card. When detecting no input for a given time from the previous input, the card processor 5a totals the amounts of money input so far, and sends the sum to the game controller 14. When a player inserts either a bill into the bill slot 30 or a coin into the coin slot 31, the money processor 5b senses the input amount of money. When detecting no input for a given time from the previous input, the money processor 5b totals the amounts of money input so far, and sends the sum to the game controller 14. Input of the amount of money and score may be accepted at all times and added to the input remaining amount and the total score.

In the embodiment, a plurality of types of game are registered in the storage 6 and a play charge is defined to be subtracted from the amount of money whenever the player plays one game. A play score is also defined to be subtracted from the total score whenever the player plays one game if the game amount of money is less than the play charge, and is registered in the storage 6. The one game refers to the time interval from display of a pinball image to disappearance thereof for a pinball game or from start of reel rotation to stop thereof for a slot machine game. For other games, one game is previously defined for each game type.

When receiving the information, the game controller 14 checks whether or not the input amount of money is equal to or greater than the lowest one of all registered game play charges at step 112. If it is greater than the lowest play charge, the game controller 14 sets the input amount as the input remaining amount and displays the input remaining amount and the total score in the remaining amount display area 32 and the upper and lower score display areas 37 and 35 on the display unit 10 at step 117. If the total score is equal to or greater than the lowest play score although the input amount is less than the lowest play charge, the embodiment allows the player to play a game. Then, if the total score input is equal to or greater than the lowest play score at step 113, the game controller 14 advances to step 117. If it is less than the lowest play score, the game controller 14 displays a message indicating that the input amount is insufficient to play a game, on the game image display unit 11 through the image display controller 15 at step 114, and accepts an input from the player through the game interface 16. If the player inputs a cancel command by pressing the cancel switch 24 or an adjustment command by pressing the adjustment switch 27 at step 115, it means that the player abandons playing a game. Then, the game controller 14 performs an adjustment process at step 116 and returns to the initial state at step 110. If neither a cancel command nor an adjustment command is input, the game controller 14 returns to step 110, to wait for a player to input an amount of money.

Figure 14:
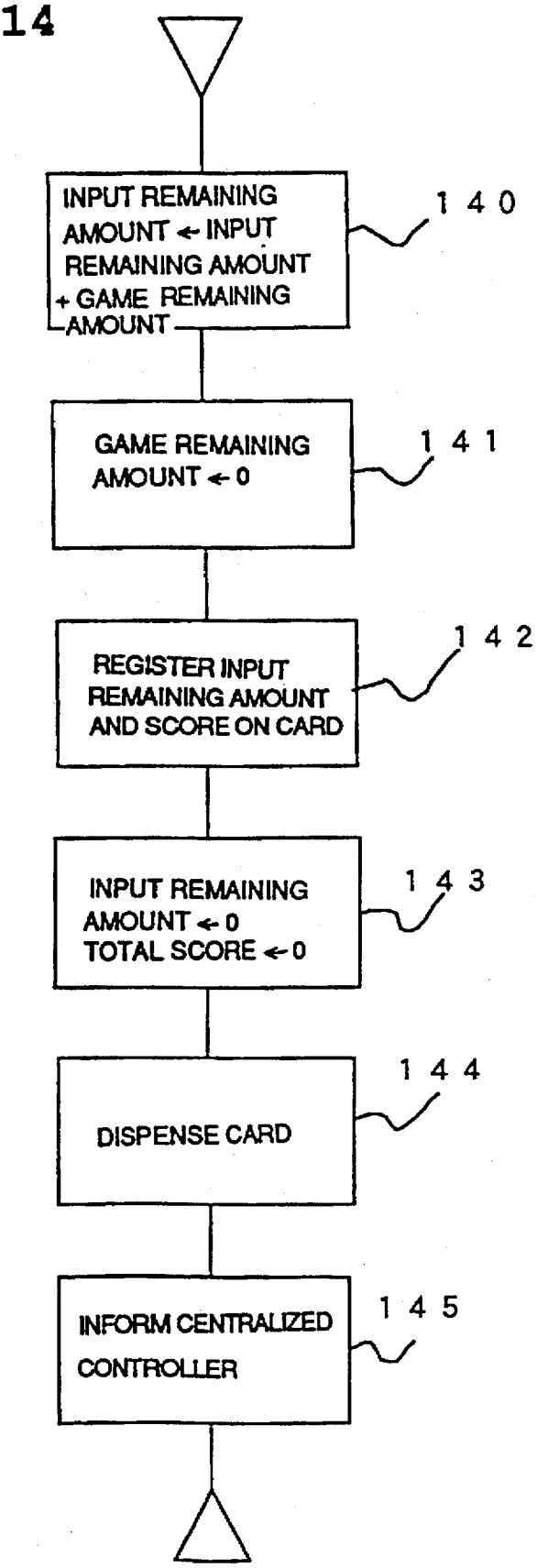
FIG. 14 is a flowchart showing an adjustment process of the game controller.

FIG. 14 shows the adjustment process. In the adjustment process, the game controller 14 adds the game remaining amount to the input remaining amount at step 140 and sets the game remaining amount to the initial value 0 at step 141. Further, the game controller 14 causes the card processor 5a to register (magnetically record or print) the input remaining amount after the addition, and the score, on a predetermined card (if the player inputs a card in place of cash, on that card; if the player does not input a card, on a card held in the card stack section of the card processor 5a) at step 142, sets the input remaining amount and the total score to the initial values 0 at step 143, and causes the card processor 5a to dispense the card through the card inlet/outlet 29 at step 144. Lastly, the game controller 14 informs the centralized controller 50 that adjustment has been made at step 145. At this time, data of the total score, the adjustment time, the time for which the gaming machine 1 was occupied, etc., may be sent to the centralized controller 50. At the time of adjustment, a system charge may be collected from the score or input remaining amount.

The embodiment allows the player to exchange the dispensed card for a prize or to input the card to another gaming machine 1 for again playing a game. The game controller 14 also performs processing similar to the adjustment process mentioned above in the adjustment process described in the game remaining amount and degree-of-difficulty update process (step 1030) below.

(2) Game remaining amount determination process (step 101)

When the input remaining amount and the score are determined, the game controller 14 performs a game remaining amount determination process at step 101.

Figure 12:
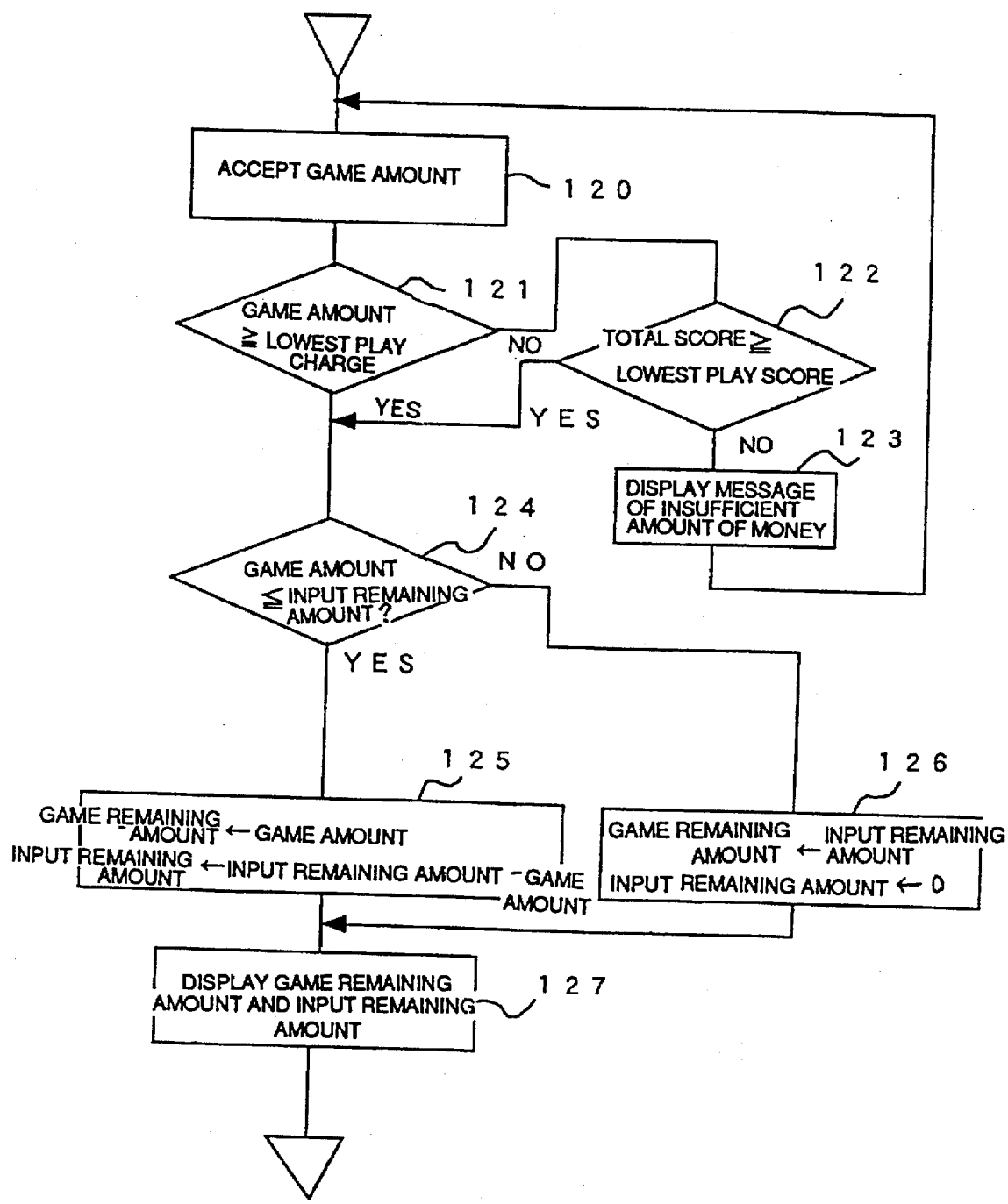
FIG. 12 is a flowchart showing a game remaining amount determination process of the game controller.

FIG. 12 shows the game remaining amount determination process. First, the game controller 14 accepts the amount of money spent for playing a game, specified by a player operating the game amount selection switch 25 via the game interface 16. The game controller 14 checks whether or not the input game amount is equal to or greater than the lowest play charge at step 121. If it is less than the lowest play charge, the game controller 14 checks whether or not the total score is equal to or greater than the lowest play score at step 122. If it is less than the lowest play score, the game controller 14 displays a message indicating that the game amount is insufficient to play a game on the game image display unit 11 through the image display controller 15 at step 123, and returns to step 120.

At step 124, if the input game amount is equal to or greater than the lowest play charge, the game controller 14 checks whether or not the game amount is equal to or less than the input remaining amount determined at step 100. If it is equal to or less than the input remaining amount, the game controller 14 sets the game amount as the game remaining amount and subtracts the game amount from the input remaining amount at step 125. If the game amount is greater than the input remaining amount, the game controller 14 sets the input remaining amount as the game remaining amount and sets the input remaining amount to 0 at step 126. In either case, the game controller 14 finally displays the game remaining amount and the input remaining amount in the game remaining amount display area 33 and the input remaining amount display area 32.

(3) Game selection process (step 102)

Figure 13:
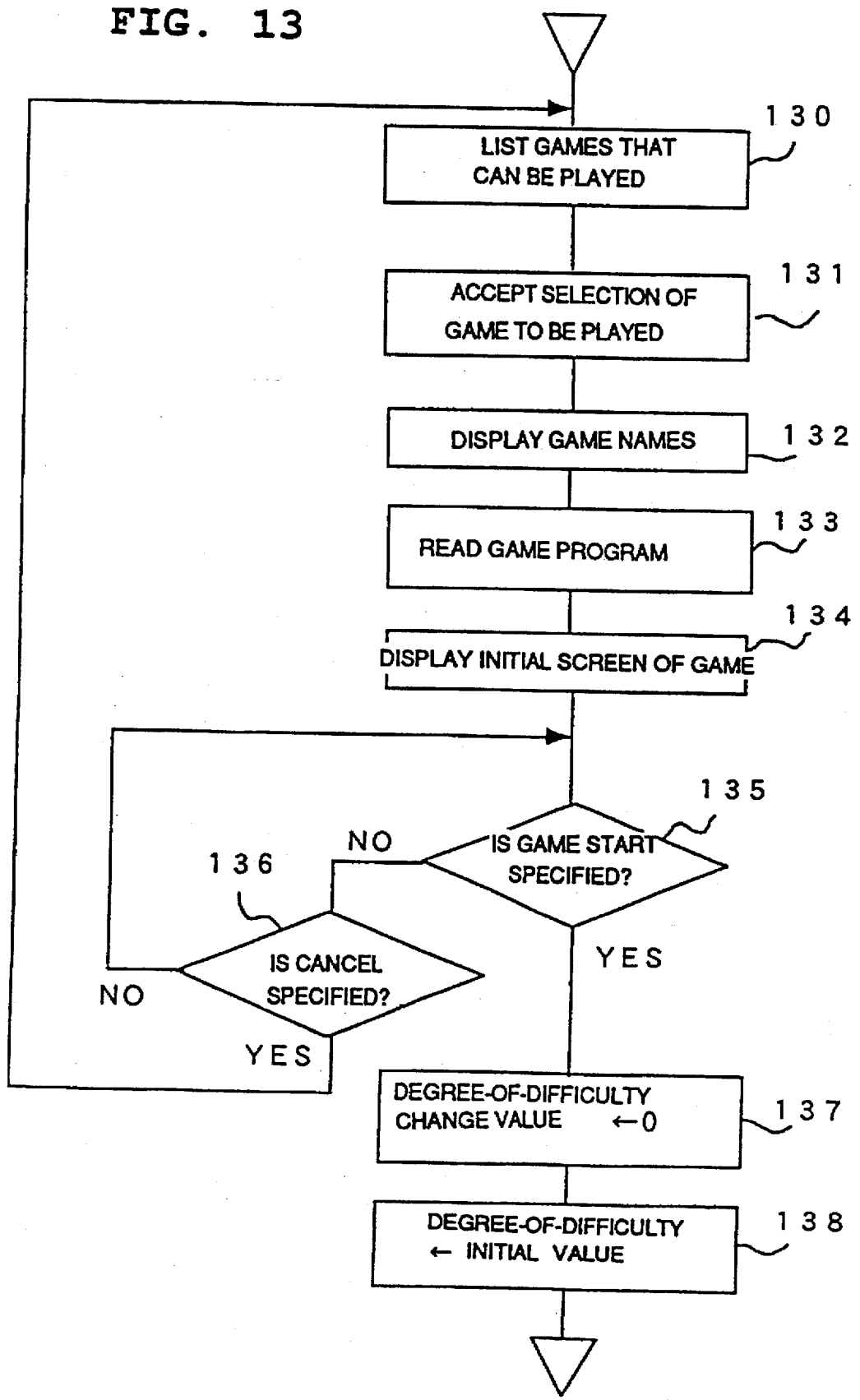
FIG. 13 is a flowchart showing a game selection process of the game controller.

Next, the game controller performs a game selection process for accepting selection of a game to be played at step 102. FIG. 13 shows a flow of the game selection process.

First, the game controller searches the game memory 12 in which games are registered for types of games that can be played within the game amount (game remaining amount) determined in the game remaining amount determination process at step, 101 and total score and displays a menu of the games that can be played (a list of the game names) and a cursor or the like for pointing to a specific game on the menu on the game image display unit 11 through the image display controller 15 at step 130.

When sensing that the player handles the main switch 21 on the operation section 5 via the game interface 16, the game controller 14 moves the position (game name) pointed to by the cursor to the side where the main switch 21 is operated and when the player operates the setting switch 23, the game controller 14 judges that the game pointed to by the cursor is selected at step 131.

Next, the game controller 14 displays the specified game name in the upper and lower game name display areas 36 and 34 on the display unit 10 at step 132, reads the program of the selected game from the game memory 12 at step 133, and displays a predetermined initial screen of the game at step 134. If the selected program is for pinball games, for example, the initial screen provides a pinball base board image as shown in FIG. 8; if the selected program is for slot machine games, for example, the initial screen provides a slot image as shown in FIG. 9. There are also predetermined initial screens for other video games.

When detecting via the game interface 16 the player pressing the cancel switch 24 before operating the handle 26 or the like for specifying the game start at step 135, the game controller 14 returns control to step 130 for repeating the game selection process at step 136, whereby the player can see the initial screens before determining which game to play, and again select a game from the beginning. The game controller 14 accepts a game start command via the game interface 16 when the player operates the handle 26 for pinball and slot machine games or when the player operates the switch determined for each game type for other video games.

If the player specifies the game start before pressing the cancel switch 24 as a cancel command at step 135, the game controller 14 assigns the initial value 0 to the degree-of-difficulty change value used to change the degree of difficulty in playing a game at step 137 and sets the degree of difficulty to the initial value determined for each game type at step 138.

(4) Game remaining amount and degree-of-difficulty update process (steps 1031–1038)

When the player selects the game type and specifies the game start, the game controller 14 updates the game remaining amount and the degree of difficulty at steps 1031 to 1038.

First, the game controller 14 checks whether or not the game remaining amount is equal to or greater than the play charge of the selected game at step 1031. If it is equal to or greater than the play charge, the game controller 14 subtracts the 1- game play charge from the game remaining amount and displays the updated game remaining amount in the game remaining amount display area 33 at step 1038, then adds the degree-of-difficulty change value to the degree of difficulty for setting a new degree of difficulty at step 1039.

If the game remaining amount is less than the play charge, the game controller 14 checks whether or not the total score is greater than or equal to the play score of the selected game at step 1032. If the total score is equal to or greater than the play score, the game controller 14 subtracts the play score from the total score and displays the updated total score in the upper and lower score display areas 37 and 35 at step 1037, then advances to step 1039 described above. If the total score is less than the play score, the player cannot play the selected game. Then, the game controller 14 displays a message indicating that the game remaining amount is insufficient to play the game on the game image display unit 11. It also displays a game selection change, game amount change, input amount change, adjustment, and cursor as a menu for the subsequent process and accepts cursor move commands from the main switch on the operation section 5 and a selection determination from the setting switch 23 at step 1033 as in the game selection acceptance at step 131 in the game selection process.

If the selected menu item is the game selection change, the game controller 14 returns control to step 102 at step 1034; if it is the game amount change, returns control to step 101 at step 1035; if it is the input amount change, returns control to step 100 at step 1036; or if it is the adjustment, performs an adjustment process at step 1030, then returns control to step 100.

(5) Game execution (steps 104–106)

Upon determination of the degree of difficulty at step 1039, the game controller 14 uses the determined degree of difficulty to execute one game of the selected type at step 104. The game controller 14 keeps the game execution start time and end time.

In execution of one game, if the selected game is a pinball game, the game controller 14, when detecting the player rotating the handle 26 through the game interface 16, displays the moving image of a pinball propelled at the speed corresponding to the rotation amount on the pinball base board displayed on the game image display unit 11 at step 134 of the game selection process until the pinball image disappears from the base board. At this time, the degree of difficulty is used to determine the probability of entering a special win condition if the pinball image enters the hole of the win effect indication 84b; it is previously defined by the game program so that the higher the degree of difficulty, the lower the probability. The number of holes, which allows the special win condition to be entered if the pinball image enters the hole, may be increased according to the degree of difficulty.

On the other hand, if the selected program is a slot machine game, the game controller 14 displays reel images in the slots displayed on the game image display unit 11 at step 134, and when detecting the player pressing the handle 26 through the game interface 16, displays a moving picture on which the drums rotate. When detecting the player operating the game end switch 38, the game controller 14 stops the moving picture of the rotating drums. In the slot machine game, the position at which a score is added when a predetermined symbol pattern is completed (one horizontal row at the middle stage, one horizontal row at the top, middle, or bottom stage, or one slant row) is defined depending on the number of input coins (or equivalent amount of money or score). In the slot machine game, the degree of difficulty is used to determine the symbol pattern occurrence frequency. It is previously defined by the game program so that the higher the degree of difficulty, the lower the occurrence frequency.

If a game like a general video game is selected, the game controller 14 displays the game image on the game image display unit 11, and makes the programmed game progress in response to the player operating the switches predetermined for each game type. Use of the degree of difficulty is previously defined for each game type; it is used to determine variables defined for each game type, for example, the number of player home balls (the higher the degree of difficulty, the fewer the number of home balls), frequency of attack from an enemy (the higher the degree of difficulty, the higher the attack frequency), enemy character life force (the higher the degree of difficulty, the greater the number of attack times needed to defeat the enemy), player character life force (the higher the degree of difficulty, the fewer is the number of attack times needed for the player army to be defeated by the enemy), attack effect (the higher the degree of difficulty, the narrower the hit range), etc., in shooting games. In puzzle games in which problems are registered for each degree of difficulty, one of a number of puzzles registered as having the determined degree of difficulty is extracted at random. Alternatively, in puzzle games, the time limit for solving a given puzzle may be changed so that the higher the degree of difficulty, the shorter the time limit.

In the game execution, if the player gains some points, the game controller 14 adds the gained points to the total score and displays the new total score in the upper and lower score display areas 37 and 35 on the display unit 10 at step 105. The played 1-game score and the total score may be displayed in the upper and lower score display areas 37 and 35 respectively.

Next, the game controller 14 informs the centralized controller 50 of the game progress conditions of the selected game type, the current degree of difficulty, the game start time, the game end time, and the score of the game gained by the player. When receiving the information, the centralized controller 50 returns a degree-of-difficulty change value or a termination instruction to the game controller 14 of the gaming machine 1. If the game controller 14 receives the degree-of-difficulty change value, it sets the value returned from the centralized controller 50 as a new degree-of-difficulty change value; if the game controller 14 receives no degree-of-difficulty change value, it sets the initial value 0 as a new degree-of-difficulty change value at step 106. This query and response sequence to and from the centralized controller 50 may be performed every given number of times, for example, once every 10 times, rather than every game. In this case, the progress conditions of games played the given number of times are stored in the storage.

On the other hand, if the game controller 14 receives the termination instruction at step 107, it displays a termination message such as "TERMINATION" or "GIVE UP . . . " on the game image display unit 11 at step 1071, performs adjustment processing at step 1030, and returns control to the initial state (step 100).

When no termination instruction is given, if the player inputs an adjustment command by operating the adjustment switch 27 at step 108, the game controller 14 performs adjustment processing at step 1030, and returns control to the initial state (step 100); if the player inputs a cancel command by operating the cancel switch 24 at step 109, the game controller 14 returns control to the game remaining amount determination process (step 101). If the player handles any other switch such as the game switch 22 or the handle 26, the game controller 14 returns control to step 1031 for enabling the player to repeat playing a game so long as the game remaining amount or the total score satisfies the play charge or the play score.

II. Process flow of centralized controller 50

Figure 19:
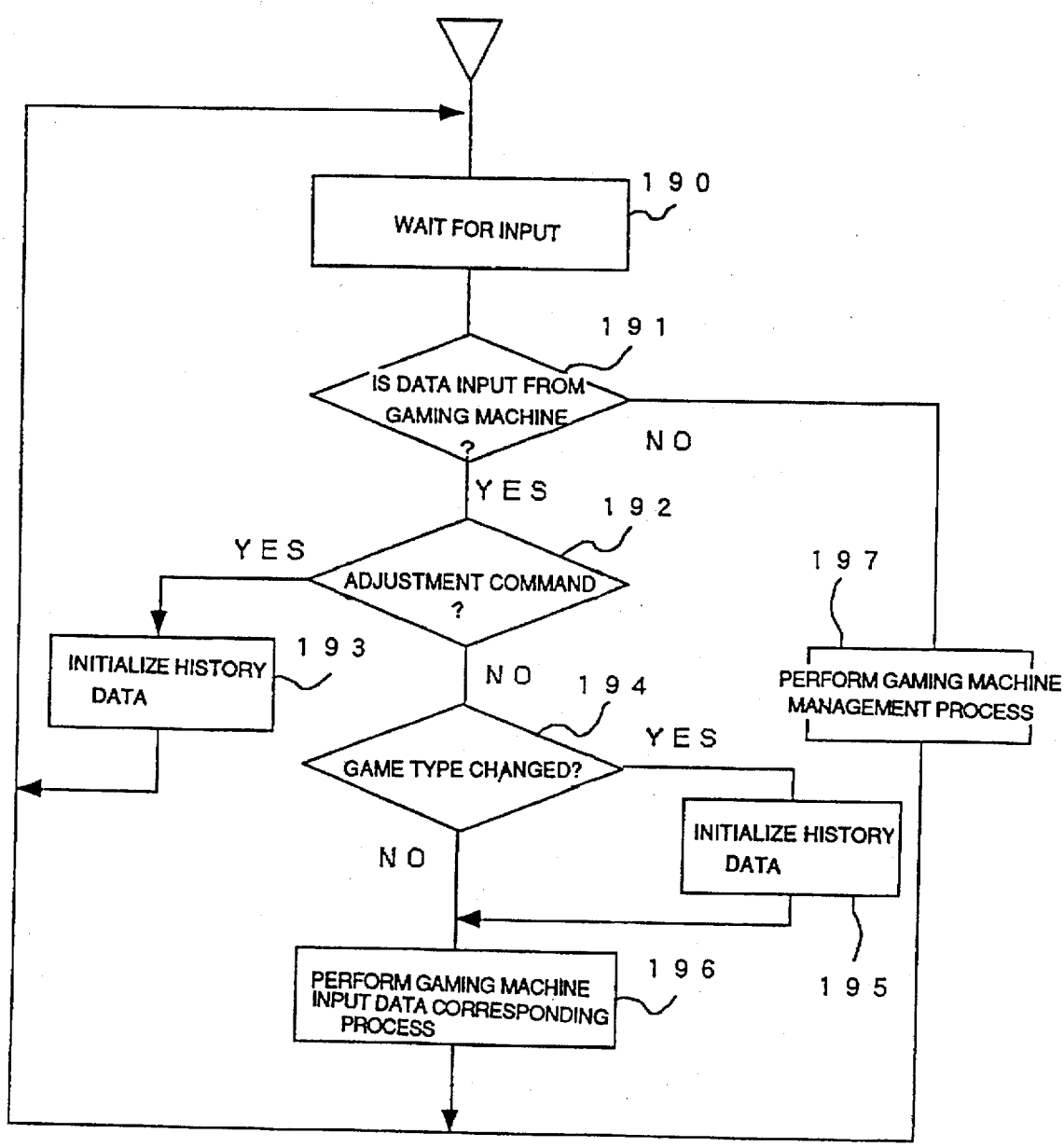
FIG. 19 is a flowchart showing the processing contents of the game monitor section.

Next, a process flow of the centralized controller 50 will be discussed. In the centralized controller 50, the game monitor section 53 uses input data from each gaming machine 1 or the input/output unit 42 to perform centralized management processing for the gaming machines 1. FIG. 19 shows a process flow of the game monitor section 53.

In the initial state, the game monitor section 53 waits for input from each gaming machine 1 or the input/output unit 42 at step 190. When receiving input from a gaming machine 1 at step 191, the game monitor section 53 checks whether or not the input is an adjustment command at step 192. If it is an adjustment command, the game monitor section 53 initializes the history data of the gaming machine 1 in the memory 52.

If it is not an adjustment command, the game monitor section 53 checks whether or not the game type in the history data held in the memory 52 matches the game type contained in the input data at step 194. If the game type remains the same, the game monitor section 53 performs a gaming machine input data corresponding process at step 196 and returns to the initial state (step 190). If the game type is changed, the game monitor section 53 initializes the history data of the gaming machine 1 in the memory 52 at step 195 and goes to step 196.

If the input data is not data from any gaming machine 1, it is input for managing a gaming machine 1, performed by an administrator through the input/output unit 42. Then, the game monitor section 53 executes a gaming machine management process at step 197 and returns to the initial state (step 190).

(1) Gaming machine input data corresponding process (step 196)

Figure 15:
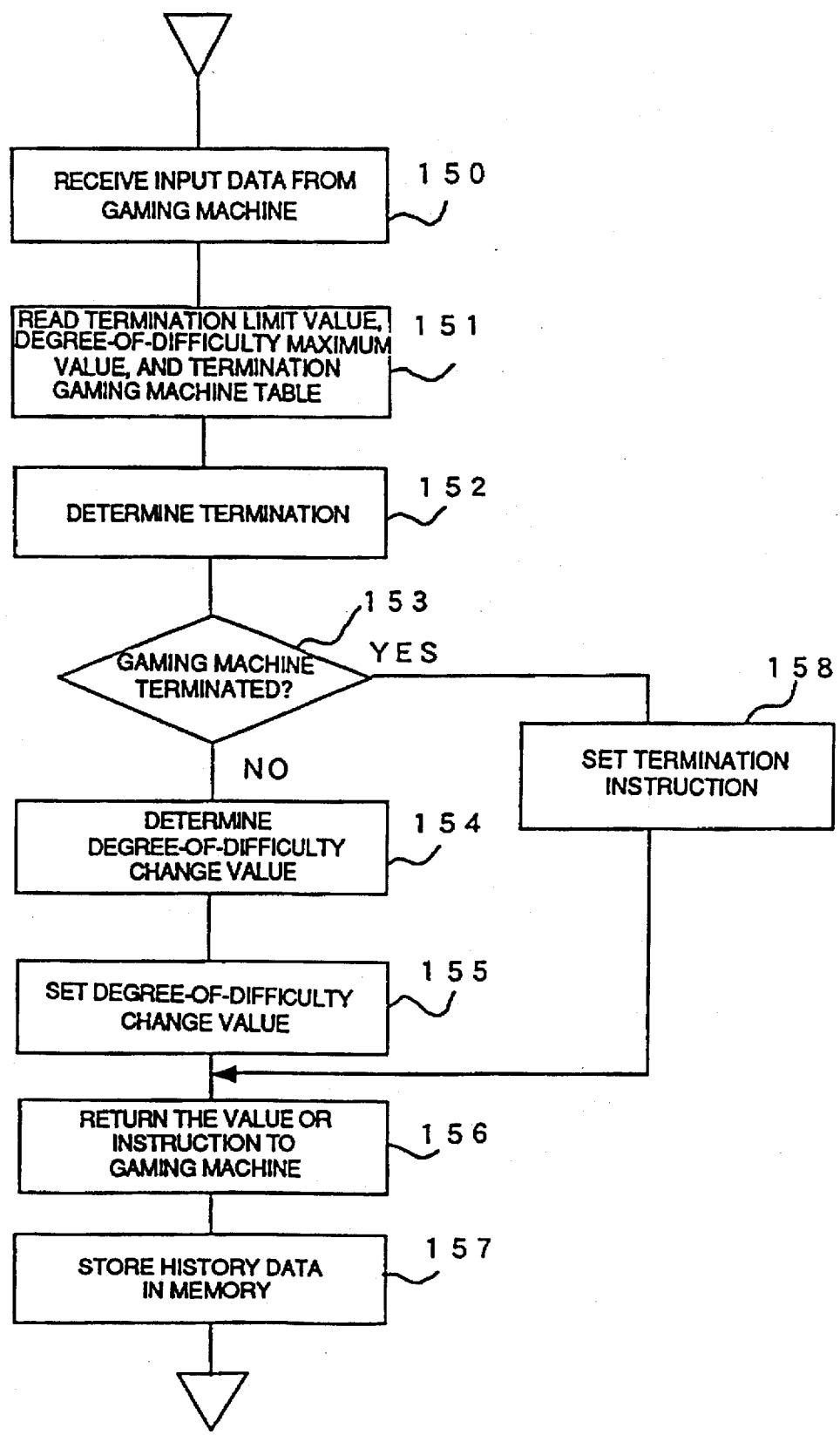
FIG. 15 is a flowchart showing a gaming machine input data corresponding process of a game monitor section.

FIG. 15 shows a process in which the game monitor section 53 receives a game condition signal from the game controller 14 of each gaming machine 1 through the communication controller 51 and returns a degree-of-difficulty change value or a termination instruction to each gaming machine 1 through the communication controller 51.

First, the game monitor section 53 receives input data of the selected game type, the current degree of difficulty, the game start time, the game end time, and the score of the game gained by a player from the game controller 14 of a gaming machine 1 at step 150, and reads the termination limit value, which is predetermined for each game type and held in a termination limit value storage area (not shown) in the memory 52, the degree-of-difficulty maximum value, which is predetermined for each game type and held in a degree-of-difficulty maximum value storage area (not shown) in the memory 52, and a termination gaming machine table, which registers the gaming machine to be terminated and is held in a termination gaming machine table storage area (not shown) in the memory 52, at step 151. Which of the score (the limit value is represented by the score) and the playing time found by calculation from the start time and end time (the limit value is represented by the time) the termination is determined by is previously defined for each game type. In the embodiment, termination in games such as pinball and slot machine games is determined by the score; termination in games such as some shooting games and puzzle games is determined by the time.

Next, the game monitor section 53 causes the gaming machine termination controller 55 to determine whether or not the gaming machine is to be terminated at step 152. When terminating the gaming machine, the gaming machine termination controller 55 returns 1 to the argument; when not terminating the gaming machine, it returns 0 to the argument. The game monitor section 53 uses the argument to judge whether or not the gaming machine is determined to be terminated at step 153.

When the gaming machine is determined to be terminated, namely, when 1 is returned to the argument, the game monitor section 53 sets a termination instruction at step 158 and advances to step 156 for returning it through the communication controller 51 to the game controller 14 of the gaming machine 1 sending the input data.

When the gaming machine is not determined to be terminated, namely, i.e. when 0 is returned to the argument, the game monitor section 53 may change the degree of difficulty. Then, the game monitor section 53 causes the degree-of-difficulty adjustment section 54 to determine a degree-of-difficulty change value at step 154, sets the determined degree-of-difficulty change value at step 155, and returns it through the communication controller 51 to the game controller 14 of the gaming machine 1 sending the input data at step 156. The game monitor section 53 may previously determine whether or not the degree of difficulty needs to be changed and if it need not be changed, the determination of the degree-of-difficulty change value by the degree-of-difficulty adjustment section 54 may be skipped. The degree-of-difficulty change value may be determined each time a game has been played a given number of times rather than determination of the change value each time a game is played once. Further, the game controller 14 of each gaming machine 1 may determine whether or not the gaming machine 1 is to be terminated and send the determination result to the centralized controller, in which case the determination by the gaming machine termination controller 55 is not required.

After returning the instruction or value, the game monitor section 53 stores the score, the degree of difficulty, and the game start time and end time in the memory 52 at step 157 as the history data of the gaming machine 1 sending the input data. The determination result may be output to both or either of the display unit 57 and the printer 58; for example, if a termination instruction is given, it may be output to the printer 58. Any other data, such as the degree-of-difficulty change value and presence or absence of termination, may be stored. In the embodiment, when adjustment is made or when the type of game played is changed, the history data stored so far is initialized, but the history data may be output to the printer 58 at the time of initialization. Instead of outputting to the printer 58, an external storage unit such as a floppy disk drive may be connected for storing the history data on the external storage unit, or a new save area for the history data may be provided in the memory for storing the history data. If the history data is thus stored after the game type change or adjustment, data of the game type change time, adjustment time, presence or absence of termination, etc., may be added.

(2) Degree-of-difficulty change value determination process (degree-of-difficulty adjustment section 54)

Next, the degree-of-difficulty change value determination process of the degree-of-difficulty adjustment section 54 described above will be discussed. This process is performed in response to an inquiry made by the game monitor section 53 at step 152.

Figure 17:
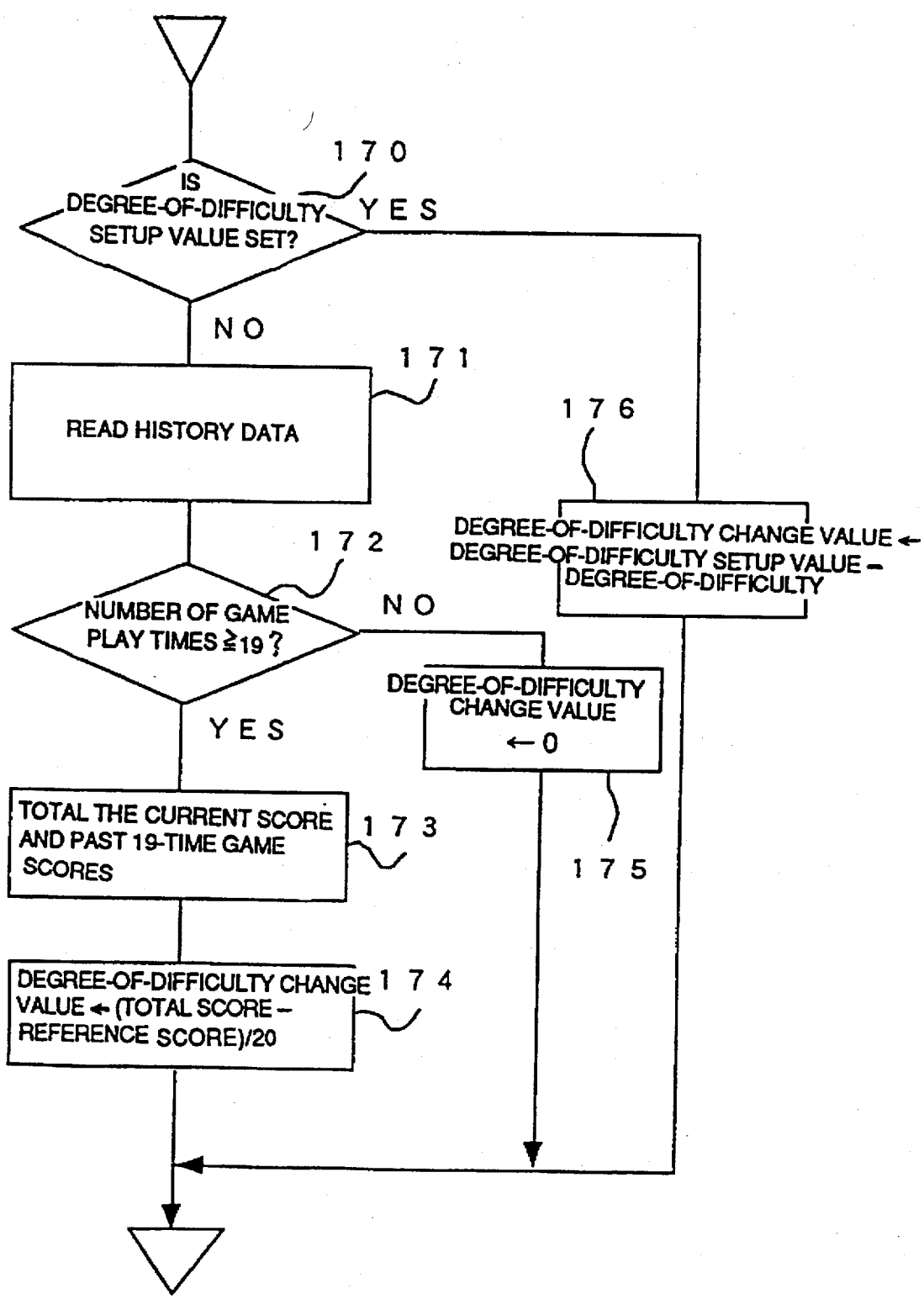
FIG. 17 is a flowchart showing a degree-of-difficulty determination process of a degree-of-difficulty adjustment section.

The degree-of-difficulty change value determination process is previously defined for each game type. For example, making the total score gained at a game played a given number of times (or the total play time) constant is possible as a degree-of-difficulty change value determination reference. FIG. 17 shows the degree-of-difficulty change value determination process in which the degree-of-difficulty change value is determined using the score as the reference and the degree of difficulty is used to determine the win probability in games such as pinball and slot machine games, for example.

First, the degree-of-difficulty adjustment section 54 checks whether or not a degree-of-difficulty setup value is set by a gaming machine management process (described below) at step 170. If it is set (the degree-of-difficulty setting flag in the memory 52 is set to 1), it indicates that the administrator instructs the degree of difficulty to be set to the degree-of-difficulty setup value. Then, the degree-of-difficulty adjustment section 54 subtracts the current degree of difficulty from the degree-of-difficulty setup value and sets the result as the degree-of-difficulty change value at step 176.

If no degree-of-difficulty setup value is set (the degree-of-difficulty setting flag in the memory 52 is set to 0), the degree-of-difficulty adjustment section 54 reads the history data (shown in FIG. 20) of the gaming machine 1 stored in the memory 52 through the game monitor section 53 at step 171. The history data contains the number of game play times held in the number-of-game-play-times storage area 200. If the number of game play times is less than 19 at step 172, the degree-of-difficulty adjustment section 54 sets the degree-of-difficulty change value to 0 at step 175, and returns control to the game monitor section 53.

If the number of game play times is equal to or greater than 19, the degree-of-difficulty totals adjustment section 54 the scores of the 19 most recent game plays of the game type held in the game data storage areas 207 of the history data storage area 207, and adds the score contained in the input data from the gaming machine 1 to the total to find the total score of 20 game plays at step 173. Next, subtracts a reference score predetermined for each game type and held in the memory 52 from the total score of the 20 game plays, divides the difference by 20, sets the result (decimals are rounded up) as the degree-of-difficulty change value at step 174, and returns control to the game monitor section 53.

Since the degree-of-difficulty change value is determined by using the reference score as the reference in pinball and slot machine games in the embodiment as described above, the reference score can be changed for changing the degrees of difficulty of all gaming machines 1 connected to the centralized controller by one operation.

The degree-of-difficulty change value determination process has been discussed as an example, and any other method for determining the degree-of-difficulty change value can be used. For example, degree-of-difficulty change values may be previously registered in the memory 52 as a table and one of the degree-of-difficulty change values can be selected out of the table in response to the input score, etc.

Although the degree-of-difficulty change value is determined by the score, etc., in the embodiment, it may be determined by the number of wins rather than the score, and the score (score rate) given to a player for one winning game play may be increased as the degree of difficulty rises. In this case, the number of wins needs to be contained in the input data from each gaming machine 1. When a game is played at the gaming machine 1, the change of the score rate needs to be considered.

(3) Termination determination process (gaming machine termination controller 55)

Figure 16:
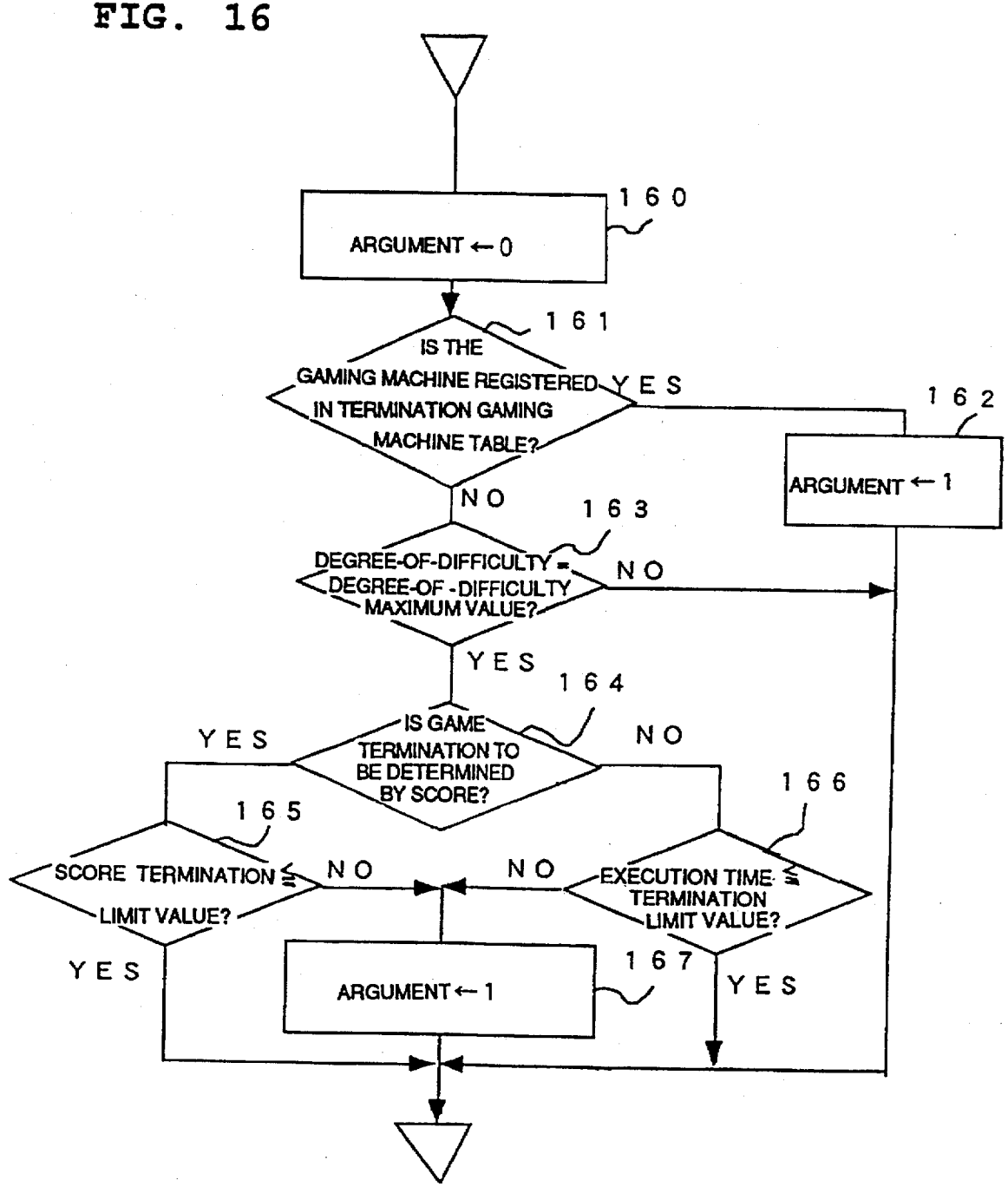
FIG. 16 is a flowchart showing a termination determination process of a gaming machine termination controller.

FIG. 16 shows a flow of a termination determination process performed by the gaming machine termination controller 55. This process is executed in response to an inquiry made by the game monitor section 53 at step 157 described above.

First, the gaming machine termination controller 55 sets the argument value to 0 at step 160, then checks whether or not the gaming machine 1 to be processed is registered in the termination gaming machine table at step 161 and if it is registered, returns argument 1 to the game monitor section 53 at step 162. If it is not registered, the gaming machine termination controller 55 checks whether or not the input degree of difficulty matches the degree-of-difficulty maximum value predetermined for each game type at step 163. If the degree of difficulty does not match the degree-of-difficulty maximum value, the gaming machine termination controller 55 makes the argument remain 0 and returns control to the game monitor section 53.

If they match, the gaming machine termination controller 55 checks whether or not the game is a game whose termination is to be determined by the score at step 164. If the game is a game whose termination is to be determined by the score, the gaming machine termination controller 55 checks whether or not the score input through the gaming machine 1 is equal to or less than the termination limit value at step 165 and only when the score is greater than the limit value, stores 1 in the argument at step 167. If the game is not a game whose termination is to be determined by the score, the gaming machine termination controller 55 checks whether or not the game execution time input through the gaming machine 1 is equal to or less than the termination limit value at step 166 and only when the game execution time is longer than the limit value, advances to step 167 and stores 1 in the argument. In either case, control is returned to the game monitor section 53.

(4) Gaming machine management process (step 197)

Figure 18:
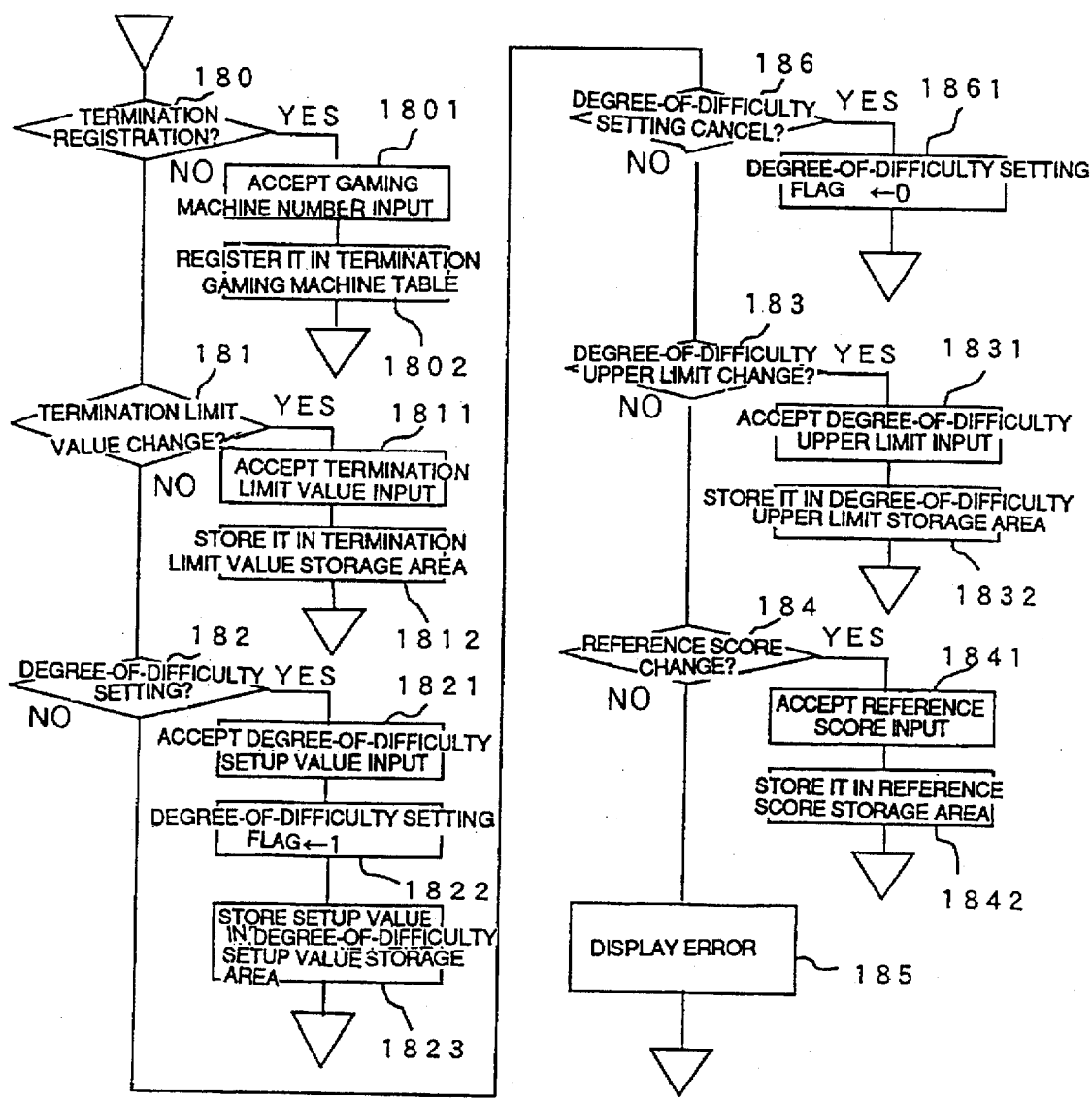
FIG. 18 is a flowchart showing a gaming machine management process of the game monitor section.

In the input wait state at step 190 described above, a management process menu is displayed on the display unit 57 of the input/output unit 42. The game monitor section 53 accepts an input of the number assigned to a management item listed on the menu by an administrator through the ten-key numerical pad 56. The game monitor section 53 has a function of controlling each gaming machine with the input from the input unit 42 by the administrator as a trigger. FIG. 18 shows a flow of the control. The menu items in the embodiment include six items of termination registration, termination limit value change, degree-of-difficulty setting, degree-of-difficulty setting cancel, degree-of-difficulty upper limit change, and reference score change, but other items may also be provided.

First, if the input item is the termination registration at step 180, the game monitor section 53 accepts the registration number, which is assigned to each gaming machine, of the gaming machine 1 to be terminated at step 1801, registers it in the termination gaming machine table in the memory 52 at step 1802, and terminates the gaming machine management process. A function of terminating all gaming machines 1 by one operation may be provided. In this case, a special flag for terminating all gaming machines 1 when a batch termination instruction is received may be stored in the termination gaming machine table and if the flag is set when the gaming machine termination controller determines termination, the gaming machines may be terminated unconditionally.

If the input item is the termination limit value change at step 181, the game monitor section 53 accepts an input of a termination limit value at step 1811. At this time, the termination limit value is determined for each game type, thus the game monitor section 53 also accepts an input of the game type for which the limit value is specified. Next, the game monitor section 53 stores the limit value in the termination limit value storage area corresponding to the specified game type in the memory 52 at step 1812 and terminates the gaming machine management process.

If the input item is the degree-of-difficulty setting at step 182, the game monitor section 53 accepts an input of a degree-of-difficulty setup value at step 1821. At this time, the degree-of-difficulty setup value is determined for each game type, thus the game monitor section 53 also accepts an input of the game type for which the value is specified. Next, the game monitor section 53 stores 1 in the degree-of-difficulty setting flag storage area in the memory 52 and at step 1822 stores the degree-of-difficulty in the setup value degree-of-difficulty setup value storage area corresponding to the specified game type in the memory 52 at step 1823 and terminates the gaming machine management process.

If the input item is the degree-of-difficulty setting cancel at step 186, the game monitor section 53 stores 0 in the degree-of-difficulty setting flag storage area in the memory 52 at step 1861 and terminates the gaming machine management process.

If the input item is the degree-of-difficulty upper limit change at step 183, the game monitor section 53 accepts an input of a degree-of-difficulty upper limit at step 1831. At this time, the degree-of-difficulty upper limit is determined for each game type, thus the game monitor section 53 also accepts an input of the game type for which the upper limit is specified. Next, the game monitor section 53 stores the upper limit in the degree-of-difficulty upper limit storage area corresponding to the specified game type in the memory 52 at step 1832 and terminates the gaming machine management process.

If the input item is the reference score change at step 184, the game monitor section 53 accepts an input of a reference score at step 1841. At this time, the reference score is determined for each game type, thus the game monitor section 53 also accepts an input of the game type for which the reference score is specified. Next, the game monitor section 53 stores the reference score in the reference score storage area corresponding to the specified game type in the memory 52 at step 1842 and terminates the gaming machine management process.

If the administrator inputs anything other than these items, the game monitor section 53 displays an error message on the display unit 57 and terminates the gaming machine management process at step 185.

In the embodiment, the information stored in the memory 52 is updated, whereby when an inquiry about the degree-of-difficulty change value is made at the game end, the update is returned. That is, in the termination registration, when a registered gaming machine 1 makes an inquiry, a termination instruction is sent to the gaming machine 1 through the communication controller 51. In the degree-of-difficulty setting, when any gaming machine 1 makes an inquiry, a degree-of-difficulty change value is sent to the gaming machine 1 through the communication controller 51 so that the degree of difficulty of the game played at the gaming machine 1 becomes the specified degree-of-difficulty setup value. In the termination limit value change, degree-of-difficulty upper limit change, or reference score change, when any gaming machine 1 makes an inquiry, the gaming machine termination controller 55 and the degree-of-difficulty adjustment section 54 use the updated values to determine whether or not the gaming machine is to be terminated and to adjust the degree-of-difficulty change value. However, without waiting for gaming machines 1 to make an inquiry about the degree-of-difficulty change value, the specification contents may be set in the gaming machines immediately after the above-mentioned input is made.

In the embodiment, the termination limit value change, degree-of-difficulty setting, degree-of-difficulty upper limit change, or reference score change is executed for all gaming machines 1 in a batch, but may be specified for each of the gaming machines 1. In this case, the setup value storage area of the termination limit value, degree-of-difficulty setup value, degree-of-difficulty upper limit, and reference score that can be specified for each gaming machine 1 is provided. When setting is accepted, specification of a gaming machine 1 is also accepted, and the setup values are stored in the storage area assigned to the specified gaming machine 1. Then, the storage area for each gaming machine 1 is referenced whenever necessary.

III. Features of the embodiment

Thus, the gaming system of the embodiment enables a player to play different types of games at one gaming machine. The degree of difficulty of a game played at a gaming machine 1 is adjusted in response to the score gained by the player, etc. Further, if the score exceeds a prescribed value although the degree of difficulty is the maximum value, the gaming machine 1 is terminated. Further, in the gaming system of the embodiment, information on termination, degree of difficulty, etc., of gaming machines 1 can be input to the centralized controller 50 for batch management.

Embodiment 2

Figure 4:
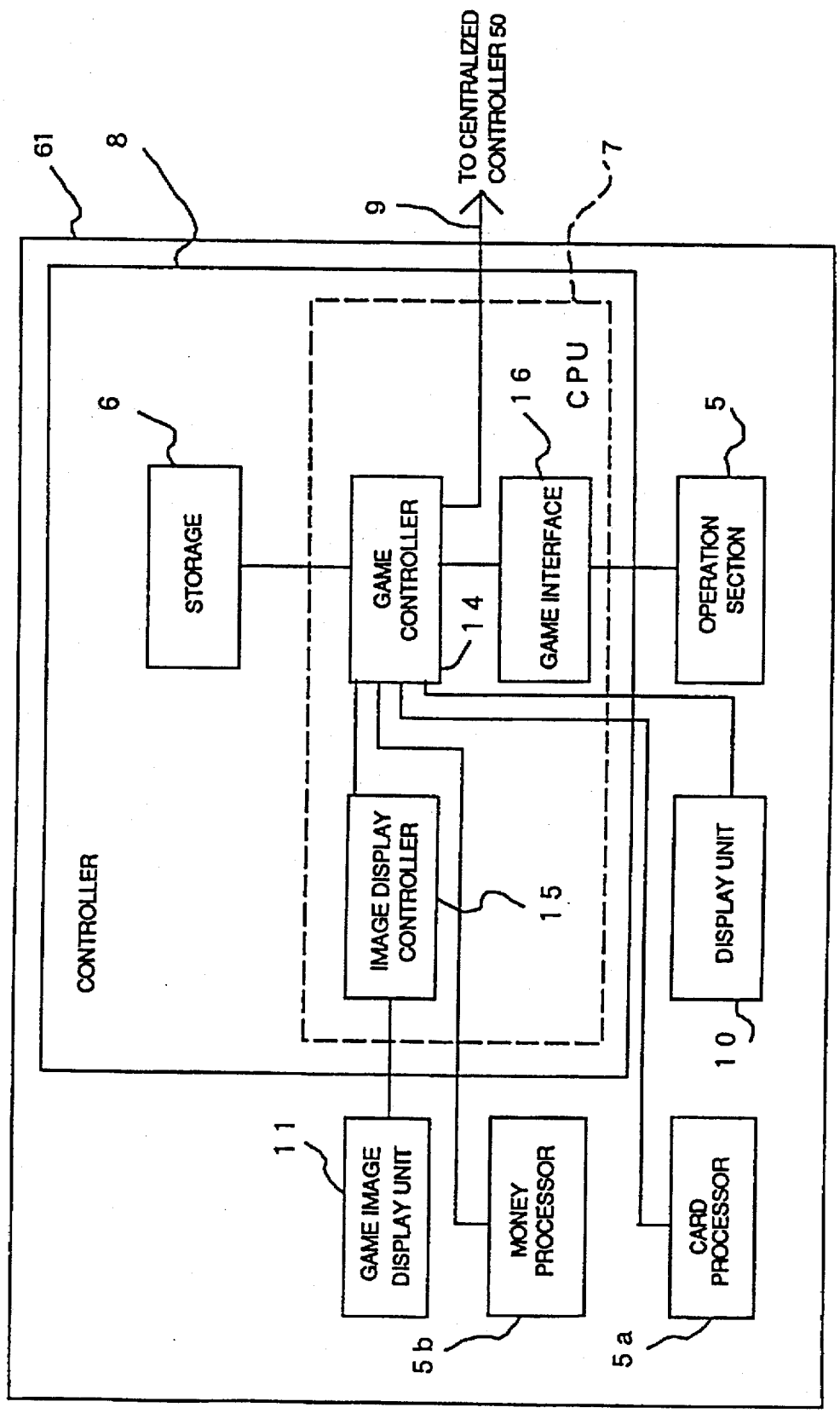
FIG. 4 is a block diagram showing the configuration of a gaming machine having no game memory.
Figure 5:
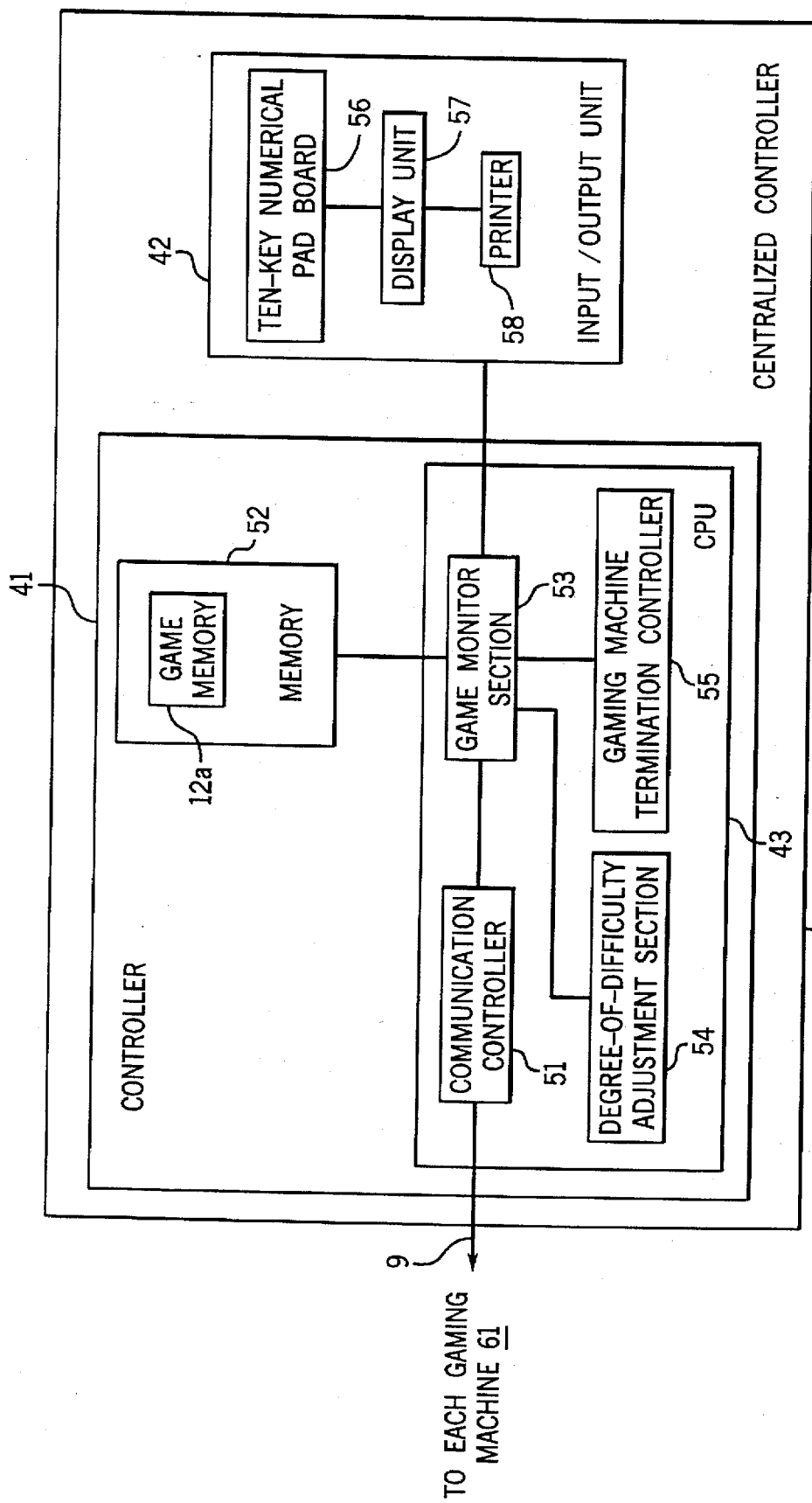
FIG. 5 is a block diagram showing the configuration of a centralized controller having a game memory.

Next, a second embodiment of the invention will be discussed. FIGS. 4 and 5 respectively show the configuration of a gaming machine and the configuration of a centralized controller in a gaming system of the embodiment. Components identical with or similar to those previously described in the first embodiment are denoted by the same reference numerals in FIGS. 4 and 5 and explanations will be omitted.

The gaming system of the embodiment is characterized by the fact that game programs are registered in the centralized controller 70 rather than in each gaming machine 61. Thus, various game programs are registered in the centralized controller in a batch; when the system is constructed, time and labor for registering the programs in each gaming machine can be saved and management of program maintenance, registration change, etc., after the system construction is facilitated. Since it is not necessary to provide the game memory 12 in the first embodiment for the gaming machines 61, each gaming machine may have a small-capacity storage.

The gaming machine 61 of the embodiment has a storage 6, which does not have the game memory 12, as shown in FIG. 4. Instead, the centralized controller 70 of the embodiment has a memory 52 provided with a game memory 12a which stores various game programs, as shown in FIG. 5.

A game controller 14 of the gaming machine 61 of the embodiment requests a game program from the centralized controller 70 instead of reading the game program from the game memory 12 at step 133 (shown in FIG. 13) in the game selection process (step 102). A game monitor section 53 of the centralized controller 70 reads the game program from the game memory 12a in response to the request input through a communication controller and transmits the game program to the gaming machine 61 requesting it.

In the first and second embodiments, the memory storing the game programs is installed in either the gaming machine or the centralized controller, but as a compromise between the configurations, both the gaming machine and the centralized controller may be provided with the game program storing memory.

In this case, the game memory of the gaming machine preferably has a small capacity and stores only popular and often executed programs and the game memory of the centralized controller stores all programs and only when the selected program is not stored in the game memory of the gaming machine, is it transmitted from the centralized controller. Thus, for frequently played games, the time required for transmitting the game programs can be saved, enabling players to play the games immediately, and compared with the case where all programs are registered in each gaming machine, the memory capacity decreases as a whole and the time and labor for program registration or maintenance is also reduced.

In the embodiments, the player can insert cash or a card into a gaming machine for playing a game, but the player may pay out cash, etc., to the administrator, who then operates the centralized controller for enabling the player to play a game at a specific gaming machine. Further, the player can also select a game by asking the administrator for a desired game without operating the gaming machine, then the administrator operates the centralized controller for enabling the player to play the game at a specific gaming machine.

What is claimed is:

1. A gaming system comprising:

a centralized controller having a controller and a storage; and at least one gaming machine connected to the centralized controller by a line, said gaming machine comprising a controller for controlling said gaming machine, a game image display unit for outputting a game image, an operation section for accepting various operation commands inputted by a player for playing a game, and a storage comprising a storage area for game programs, said controller of said gaming machine comprising:

a game controller for controlling a game;

an image display controller for outputting information, as instructed from said game controller, to said game image display unit; and a game interface for sending commands inputted to said operation section to said game controller, said operation section having means for accepting selection of a game type and informing said game controller of the selected game type, said game controller comprising:
means for determining a degree of difficulty in playing a game;
means for executing a game at the degree of difficulty;
means for informing said centralized controller of game conditions;
means for reading a game program previously stored in said storage corresponding to the game of the type selected through said operation section and executing it;
means for requesting said centralized controller to send the game program of the game of the type selected if the game program is not stored in the storage area for game programs in said gaming machine; and
means for executing the transmitted game program, said storage of said centralized controller having a central game program storage area, said controller of said centralized controller comprising:
means for accepting input of a game condition;
means responsive to the accepted game condition for determining a degree-of-difficulty change value used to determine the degree of difficulty;
means for informing said game controller of the determined degree-of-difficulty change value; and
means responsive to the request received from said game controller for reading the game program previously stored in the game program storage area of said centralized controller and transmitting the game program to said game controller.

2. The gaming system as claimed in claim 1 wherein said centralized controller further includes an input unit, wherein said storage of said centralized controller has a degree-of-difficulty setup value storage area for registering a degree-of-difficulty setup value, and wherein said controller of said centralized controller further includes:

means for determining a degree-of-difficulty change value so that the degree of difficulty becomes a degree-of-difficulty setup value stored in said degree-of-difficulty setup value storage area; and means for accepting specification of a degree-of-difficulty setup value from said input unit and storing it in said degree-of-difficulty setup value storage area.

3. The gaming system as claimed in claim 1 wherein said centralized controller further includes an input unit, wherein said storage of said centralized controller has:

a termination gaming machine table for registering the gaming machine to be terminated; and a degree-of-difficulty setup value storage area for registering a degree-of-difficulty setup value, wherein said controller of said centralized controller further includes:

means responsive to the accepted game condition for determining whether or not the gaming machine is to be terminated;

means for sending a termination instruction to said game controller in response to the determination of termination;

means for sending a termination instruction to said game controller of the gaming machine registered in said termination gaming machine table;

means for accepting specification of the gaming machine to be terminated from said input unit and registering the gaming machine in said termination gaming machine table;

means for determining a degree-of-difficulty change value so that the degree of difficulty becomes a degree-of-difficulty setup value stored in said degree-of-difficulty setup value storage area; and means for accepting specification of a degree-of-difficulty setup value from said input unit and storing it in said degree-of-difficulty setup value storage area, said game controller having means for terminating said gaming machine upon receipt of the termination instruction, wherein said means for informing said centralized controller of game conditions is means for informing said centralized controller of a game condition containing at least one of either a score gained by a player playing a game or game playing time, said means for determining a degree-of-difficulty change value being means for determining the degree-of-difficulty change value using a difference between at least one of either the score or the game playing time contained in the received game condition and a predetermined reference value, said means for informing said centralized controller of game conditions being means for informing said centralized controller of a game condition containing at least one of a score gained by a player playing a game, game playing time, and the degree of difficulty of the played game, said means for determining whether or not the gaming machine is to be terminated being means for determining whether or not the gaming machine informing said centralized controller of the game condition is to be terminated by comparing either the score or the game playing time with a predetermined termination limit value if the degree of difficulty matches a predetermined maximum value, wherein said storage of said gaming machine has a game registration area which holds at least one predetermined game name and play charges and play scores, which are predetermined corresponding to the game names, said game controller having means for instructing said image display controller to output game names with a predetermined game amount of money to be spent equal to or greater than the play charge and those with a predetermined total score equal to or greater than the play score, among the game names registered in said game registration area, and wherein said operation section has means for accepting selection of the type of game to be played from among the games outputted to said game image display unit by said image display controller and informing said game controller of the selected game type, said game controller further including means for executing the game of the type selected.

4. The gaming system as claimed in claim 1 wherein said means for informing said centralized controller of game conditions is means for informing said centralized controller of a game condition containing at least one of either a score gained by a player playing a game or game playing time, and wherein said means for determining a degree-of-difficulty change value is means for determining the degree-of-difficulty change value using at least either the score or the game playing time contained in the received game condition.

5. The gaming system as claimed in claim 4 wherein said means for determining a degree-of-difficulty change value is means for determining the degree-of-difficulty change value using a difference between at least one of either the score or the game playing time and a predetermined reference value.

6. A gaming system comprising:

a centralized controller having a controller and a storage; and at least one gaming machine connected to the centralized controller by a line, said gaming machine comprising a controller for controlling said gaming machine, a game image display unit for outputting a game image, and an operation section for accepting various operation commands inputted by a player for playing a game, said controller of said gaming machine comprising:

a game controller for controlling a game;

an image display controller for outputting information, as instructed from said game controller, to said game image display unit; and a game interface for sending commands inputted to said operation section to said game controller, said game controller comprising:

means for determining a degree of difficulty in playing a game;

means for executing a game at the degree of difficulty;

means for informing said centralized controller of game conditions; and means for terminating said gaming machine upon receipt of the termination instruction from said centralized controller, said means for informing said centralized controller of game conditions being means for informing said centralized controller of a game condition containing at least one of a score gained by a player playing a game, game playing time, and the degree of difficulty of the played game, said controller of said centralized controller comprising:

means for accepting input of a game condition;

means responsive to the accepted game condition for determining a degree-of-difficulty change value used to determine the degree of difficulty;

means for informing said game controller of the determined degree-of-difficulty change value;

means responsive to the accepted game condition for determining whether or not the gaming machine is to be terminated; and means for sending a termination instruction to said game controller in response to the determination of termination, said means for determining whether or not the gaming machine is to be terminated being means for determining whether or not the gaming machine informing said centralized controller of the game condition is to be terminated by comparing either the score or the game playing time with a predetermined termination limit value if the degree of difficulty matches a predetermined maximum value.

7. The gaming system as claimed in claim 6 wherein said centralized controller further includes an input unit, wherein said storage of said centralized controller has a termination gaming machine table for registering the gaming machine to be terminated, and wherein said controller of said centralized controller further includes:

means for sending a termination instruction to said game controller of the gaming machine registered in said termination gaming machine table; and means for accepting specification of the gaming machine to be terminated from said input unit and registering the gaming machine in said termination gaming machine table.

8. A gaming system comprising:

a centralized controller having a controller and a storage, and at least one gaming machine connected to the centralized controller by a line, said gaming machine comprises a controller for controlling said gaming machine, a game image display unit for outputting a game image, an operation section for accepting various operation commands inputted by a player for playing a game, and a storage comprising a game registration area, said game registration area being an area for holding at least one predetermined game name and play charges and play scores predetermined corresponding to the game names, said controller of said gaming machine comprising:

a game controller for controlling a game;

an image display controller for outputting information, as instructed from said game controller, to said game image display unit; and a game interface for sending commands inputted to said operation section to said game controller, said operation section having means for accepting selection of the type of game to be played from among the games to said game image display unit by said image display controller and informing said game controller of the selected game type, said game controller comprising:

means for determining a degree of difficulty in playing a game;

means for executing a game at the degree of difficulty;

means for informing said centralized controller of game conditions;

means for instructing said image display controller to output game names with a predetermined game amount of money to be spent equal to or greater than the play charge and those with a predetermined total score equal to or greater than the play score, among the game names registered in said game registration area; and means for executing the game of the type selected through said operation section, said controller of said centralized controller comprising:

means for accepting input of a game condition;

means responsive to the accepted game condition for determining a degree-of-difficulty change value used to determine the degree of difficulty; and means for informing said game controller of the determined degree-of-difficulty change value.

* * * * *